United States Patent
Vidlund et al.

(10) Patent No.: US 10,555,718 B2
(45) Date of Patent: Feb. 11, 2020

(54) APPARATUS AND METHODS FOR ALIGNMENT AND DEPLOYMENT OF INTRACARDIAC DEVICES

(71) Applicant: Tendyne Holdings, Inc., Roseville, MN (US)

(72) Inventors: Robert M. Vidlund, Forest Lake, MN (US); Craig A. Ekvall, East Bethel, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 506 days.

(21) Appl. No.: 15/085,229

(22) Filed: Mar. 30, 2016

(65) Prior Publication Data

US 2016/0206280 A1 Jul. 21, 2016

Related U.S. Application Data

(63) Continuation of application No. PCT/US2014/061046, filed on Oct. 17, 2014.
(Continued)

(51) Int. Cl.
*A61B 8/14* (2006.01)
*A61B 8/08* (2006.01)
(Continued)

(52) U.S. Cl.
CPC .......... *A61B 8/0841* (2013.01); *A61B 8/0883* (2013.01); *A61B 8/12* (2013.01);
(Continued)

(58) Field of Classification Search
CPC ..... A61B 8/483; A61B 8/488; A61B 17/0469; A61B 17/3403; A61B 17/3468;
(Continued)

(56) References Cited

U.S. PATENT DOCUMENTS 2,697,008 A 12/1954 Rowley
3,409,013 A 11/1968 Berry
(Continued)

FOREIGN PATENT DOCUMENTS

CN 1486161 3/2004
CN 1961845 A 5/2007
(Continued)

OTHER PUBLICATIONS

US 9,155,620 B2, 10/2015, Gross et al. (withdrawn)
(Continued)

*Primary Examiner* — Mark D Remaly
(74) *Attorney, Agent, or Firm* — Lerner, David, Littenberg, Krumholz & Mentlik, LLP

(57) ABSTRACT

Apparatus and methods are described herein for use in the alignment and deployment of a prosthetic heart valve, such as a mitral valve. In some embodiments, an apparatus includes a tube assembly and a needle assembly configured to be received through a lumen of an outer tube member of the tube assembly. The needle assembly includes an elongate needle having a distal tip configured to be inserted through the epicardial surface of a heart. An imaging probe is coupled to a coupling member and includes an imaging element. The imaging probe is configured to provide image data associated with a location of a commissural-commissural (C-C) plane and a location of the anterior-posterior (A-P) plane of the mitral valve and the annular region of the heart such that a prosthetic mitral valve can be positioned within the heart based at least in part on the C-C plane and the A-P plane.

10 Claims, 18 Drawing Sheets

Related U.S. Application Data

(60) Provisional application No. 61/892,390, filed on Oct. 17, 2013.

(51) Int. Cl.
*A61B 8/12* (2006.01)
*A61B 8/00* (2006.01)
*A61B 17/04* (2006.01)
*A61F 2/24* (2006.01)

(52) U.S. Cl.
CPC .......... *A61B 8/445* (2013.01); *A61B 8/4488* (2013.01); *A61B 8/483* (2013.01); *A61B 8/488* (2013.01); *A61B 17/0469* (2013.01); *A61F 2/2427* (2013.01)

(58) Field of Classification Search
CPC ........... A61B 2017/00247; A61B 2017/00783; A61B 2017/3413; A61B 8/0841; A61B 8/0883; A61B 8/12; A61B 8/445; A61B 8/4488; A61F 2/242
See application file for complete search history.

(56) References Cited

U.S. PATENT DOCUMENTS

| | | |
|---|---|---|
| 3,472,230 A | 10/1969 | Fogarty et al. |
| 3,476,101 A | 11/1969 | Ross |
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,976,079 A | 8/1976 | Samuels et al. |
| 4,003,382 A | 1/1977 | Dyke |
| 4,035,849 A | 7/1977 | Angell et al. |
| 4,056,854 A | 11/1977 | Boretos et al. |
| 4,073,438 A | 2/1978 | Meyer |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,490,859 A | 1/1985 | Black et al. |
| 4,535,483 A | 8/1985 | Klawitter et al. |
| 4,574,803 A | 3/1986 | Storz |
| 4,585,705 A | 4/1986 | Broderick et al. |
| 4,592,340 A | 6/1986 | Boyles |
| 4,605,407 A | 8/1986 | Black et al. |
| 4,612,011 A | 9/1986 | Kautzky |
| 4,626,255 A | 12/1986 | Reichart et al. |
| 4,638,886 A | 1/1987 | Marietta |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,824,180 A | 4/1989 | Levrai |
| 4,829,990 A | 5/1989 | Thuroff et al. |
| 4,830,117 A | 5/1989 | Capasso |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,923,013 A | 5/1990 | De Gennaro |
| 4,960,424 A | 10/1990 | Grooters |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 4,996,873 A | 3/1991 | Takeuchi |
| 5,007,896 A | 4/1991 | Shiber |
| 5,026,366 A | 6/1991 | Leckrone |
| 5,032,128 A | 7/1991 | Alonso |
| 5,035,706 A | 7/1991 | Giantureo et al. |
| 5,037,434 A | 8/1991 | Lane |
| 5,047,041 A | 9/1991 | Sammuels |
| 5,059,177 A | 10/1991 | Towne et al. |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,201,880 A | 4/1993 | Wright et al. |
| 5,266,073 A | 11/1993 | Wall |
| 5,282,847 A | 2/1994 | Trescony et al. |
| 5,295,958 A | 3/1994 | Shturman |
| 5,306,296 A | 4/1994 | Wright et al. |
| 5,332,402 A | 7/1994 | Teitelbaum |
| 5,336,616 A | 8/1994 | Livesey et al. |
| 5,344,442 A | 9/1994 | Deac |
| 5,360,444 A | 11/1994 | Kusuhara |
| 5,364,407 A | 11/1994 | Poll |
| 5,370,685 A | 12/1994 | Stevens |
| 5,397,351 A | 3/1995 | Pavcnik et al. |
| 5,411,055 A | 5/1995 | Kane et al. |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,184 A | 9/1996 | Machiraju |
| 5,554,185 A | 9/1996 | Block et al. |
| 5,571,175 A | 11/1996 | Vanney et al. |
| 5,591,185 A | 1/1997 | Kilmer et al. |
| 5,607,462 A | 3/1997 | Imran |
| 5,607,464 A | 3/1997 | Trescony et al. |
| 5,609,626 A | 3/1997 | Quijano et al. |
| 5,639,274 A | 6/1997 | Fischell et al. |
| 5,662,704 A | 9/1997 | Gross |
| 5,665,115 A | 9/1997 | Cragg |
| 5,674,279 A | 10/1997 | Wright et al. |
| 5,697,905 A | 12/1997 | Ambrosio |
| 5,702,368 A | 12/1997 | Stevens et al. |
| 5,716,417 A | 2/1998 | Girard et al. |
| 5,728,068 A | 3/1998 | Leone et al. |
| 5,728,151 A | 3/1998 | Garrison et al. |
| 5,735,842 A | 4/1998 | Krueger et al. |
| 5,741,333 A | 4/1998 | Frid |
| 5,749,890 A | 5/1998 | Shaknovich |
| 5,756,476 A | 5/1998 | Epstein |
| 5,769,812 A | 6/1998 | Stevens et al. |
| 5,792,179 A | 8/1998 | Sideris |
| 5,800,508 A | 9/1998 | Goicoechea et al. |
| 5,833,673 A | 11/1998 | Ockuly et al. |
| 5,840,081 A | 11/1998 | Andersen et al. |
| 5,855,597 A | 1/1999 | Jayaraman |
| 5,855,601 A | 1/1999 | Bessler |
| 5,855,602 A | 1/1999 | Angell |
| 5,904,697 A | 5/1999 | Gifford, III et al. |
| 5,925,063 A | 7/1999 | Khosravi |
| 5,957,949 A | 9/1999 | Leonhardt et al. |
| 5,968,052 A | 10/1999 | Sullivan, III et al. |
| 5,968,068 A | 10/1999 | Dehdashtian et al. |
| 5,972,030 A | 10/1999 | Garrison et al. |

(56) References Cited

U.S. PATENT DOCUMENTS

| | | |
|---|---|---|
| 5,993,481 A | 11/1999 | Marcade et al. |
| 6,027,525 A | 2/2000 | Suh et al. |
| 6,042,607 A | 3/2000 | Williamson, IV et al. |
| 6,045,497 A | 4/2000 | Schweich, Jr. et al. |
| 6,063,112 A | 5/2000 | Sgro et al. |
| 6,077,214 A | 6/2000 | Mortier et al. |
| 6,099,508 A | 8/2000 | Bousquet |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,183,411 B1 | 2/2001 | Mortier et al. |
| 6,210,408 B1 | 4/2001 | Chandrasakaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,287,339 B1 | 9/2001 | Vazquez et al. |
| 6,299,637 B1 | 10/2001 | Shaolian |
| 6,302,906 B1 | 10/2001 | Goecoechea et al. |
| 6,312,465 B1 | 11/2001 | Griffin et al. |
| 6,332,893 B1 | 12/2001 | Mortier et al. |
| 6,350,277 B1 | 2/2002 | Kocur |
| 6,358,277 B1 | 3/2002 | Duran |
| 6,379,372 B1 | 4/2002 | Dehdashtian et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,537,198 B1 | 3/2003 | Vidlund et al. |
| 6,540,782 B1 | 4/2003 | Snyders |
| 6,569,196 B1 | 5/2003 | Vesely et al. |
| 6,575,252 B2 | 6/2003 | Reed |
| 6,582,462 B1 | 6/2003 | Andersen et al. |
| 6,605,112 B1 | 8/2003 | Moll |
| 6,616,684 B1 | 9/2003 | Vidlund et al. |
| 6,622,730 B2 | 9/2003 | Ekvall et al. |
| 6,629,534 B1 | 10/2003 | St. Goar et al. |
| 6,629,921 B1 | 10/2003 | Schweich, Jr. et al. |
| 6,648,077 B2 | 11/2003 | Hoffman |
| 6,648,921 B2 | 11/2003 | Anderson et al. |
| 6,652,578 B2 | 11/2003 | Bailey et al. |
| 6,669,724 B2 | 12/2003 | Park et al. |
| 6,706,065 B2 | 3/2004 | Langberg et al. |
| 6,709,456 B2 | 3/2004 | Langberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodfat et al. |
| 6,746,401 B2 | 6/2004 | Panescu |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,810,882 B2 | 11/2004 | Langberg et al. |
| 6,830,584 B1 | 12/2004 | Seguin |
| 6,854,668 B2 | 2/2005 | Wancho et al. |
| 6,855,144 B2 | 2/2005 | Lesh |
| 6,858,001 B1 | 2/2005 | Aboul-Hosn |
| 6,890,353 B2 | 5/2005 | Cohn et al. |
| 6,893,460 B2 | 5/2005 | Spenser et al. |
| 6,896,690 B1 | 5/2005 | Lambrecht et al. |
| 6,908,424 B2 | 6/2005 | Mortier et al. |
| 6,908,481 B2 | 6/2005 | Cribier |
| 6,936,067 B2 | 8/2005 | Buchanan |
| 6,945,996 B2 | 9/2005 | Sedransk |
| 6,955,175 B2 | 10/2005 | Stevens et al. |
| 6,974,476 B2 | 12/2005 | McGuckin et al. |
| 6,976,543 B1 | 12/2005 | Fischer |
| 6,997,950 B2 | 2/2006 | Chawla |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,060,021 B1 | 6/2006 | Wilk |
| 7,077,862 B2 | 7/2006 | Vidlund et al. |
| 7,087,064 B1 | 8/2006 | Hyde |
| 7,100,614 B2 | 9/2006 | Stevens et al. |
| 7,101,395 B2 | 9/2006 | Tremulis et al. |
| 7,108,717 B2 | 9/2006 | Freidberg |
| 7,112,219 B2 | 9/2006 | Vidlund et al. |
| 7,115,141 B2 | 10/2006 | Menz et al. |
| 7,141,064 B2 | 11/2006 | Scott et al. |
| 7,175,656 B2 | 2/2007 | Khairkhahan |
| 7,198,646 B2 | 4/2007 | Figulla et al. |
| 7,201,772 B2 | 4/2007 | Schwammenthal et al. |
| 7,247,134 B2 | 7/2007 | Vidlund et al. |
| 7,252,682 B2 | 8/2007 | Seguin |
| 7,267,686 B2 | 9/2007 | DiMatteo et al. |
| 7,275,604 B1 | 10/2007 | Wall |
| 7,276,078 B2 | 10/2007 | Spenser et al. |
| 7,276,084 B2 | 10/2007 | Yang et al. |
| 7,316,706 B2 | 1/2008 | Bloom et al. |
| 7,318,278 B2 | 1/2008 | Zhang et al. |
| 7,326,236 B2 | 2/2008 | Andreas et al. |
| 7,329,278 B2 | 2/2008 | Seguin et al. |
| 7,331,991 B2 | 2/2008 | Kheradvar et al. |
| 7,335,213 B1 | 2/2008 | Hyde et al. |
| 7,374,571 B2 | 5/2008 | Pease et al. |
| 7,377,941 B2 | 5/2008 | Rhee et al. |
| 7,381,210 B2 | 6/2008 | Zarbatany et al. |
| 7,381,218 B2 | 6/2008 | Schreck |
| 7,393,360 B2 | 7/2008 | Spenser et al. |
| 7,404,824 B1 | 7/2008 | Webler et al. |
| 7,416,554 B2 | 8/2008 | Lam et al. |
| 7,422,072 B2 | 9/2008 | Dade |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,500,989 B2 | 3/2009 | Solem et al. |
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,527,647 B2 | 5/2009 | Spence |
| 7,534,260 B2 | 5/2009 | Lattouf |
| 7,556,646 B2 | 7/2009 | Yang et al. |
| 7,579,381 B2 | 8/2009 | Dove |
| 7,585,321 B2 | 9/2009 | Cribier |
| 7,591,847 B2 | 9/2009 | Navia et al. |
| 7,618,446 B2 | 11/2009 | Andersen et al. |
| 7,618,447 B2 | 11/2009 | Case et al. |
| 7,621,948 B2 | 11/2009 | Herrmann et al. |
| 7,632,304 B2 | 12/2009 | Park |
| 7,632,308 B2 | 12/2009 | Loulmet |
| 7,635,386 B1 | 12/2009 | Gammie |
| 7,674,222 B2 | 3/2010 | Nikolic et al. |
| 7,674,286 B2 | 3/2010 | Alfieri et al. |
| 7,695,510 B2 | 4/2010 | Bloom et al. |
| 7,708,775 B2 | 5/2010 | Rowe et al. |
| 7,748,389 B2 | 7/2010 | Salahieh et al. |
| 7,766,961 B2 | 8/2010 | Patel et al. |
| 7,789,909 B2 | 9/2010 | Andersen et al. |
| 7,803,168 B2 | 9/2010 | Gifford et al. |
| 7,803,184 B2 | 9/2010 | McGuckin, Jr. et al. |
| 7,803,185 B2 | 9/2010 | Gabbay |
| 7,806,928 B2 | 10/2010 | Rowe et al. |
| 7,837,727 B2 | 11/2010 | Goetz et al. |
| 7,854,762 B2 | 12/2010 | Speziali et al. |
| 7,892,281 B2 | 2/2011 | Seguin et al. |

(56) References Cited

U.S. PATENT DOCUMENTS

| | | |
|---|---|---|
| 7,896,915 B2 | 3/2011 | Guyenot et al. |
| 7,901,454 B2 | 3/2011 | Kapadia et al. |
| 7,927,370 B2 | 4/2011 | Webler et al. |
| 7,931,630 B2 | 4/2011 | Nishtala et al. |
| 7,942,928 B2 | 5/2011 | Webler et al. |
| 7,955,247 B2 | 6/2011 | Levine et al. |
| 7,955,385 B2 | 6/2011 | Crittenden |
| 7,972,378 B2 | 7/2011 | Tabor et al. |
| 7,988,727 B2 | 8/2011 | Santamore et al. |
| 7,993,394 B2 | 8/2011 | Hariton et al. |
| 8,007,992 B2 | 8/2011 | Tian et al. |
| 8,029,556 B2 | 10/2011 | Rowe |
| 8,043,368 B2 | 10/2011 | Crabtree |
| 8,052,749 B2 | 11/2011 | Salahieh |
| 8,052,750 B2 | 11/2011 | Tuval et al. |
| 8,052,751 B2 | 11/2011 | Aklog et al. |
| 8,062,355 B2 | 11/2011 | Figulla et al. |
| 8,062,359 B2 | 11/2011 | Marquez et al. |
| 8,070,802 B2 | 12/2011 | Lamphere et al. |
| 8,109,996 B2 | 2/2012 | Stacchino et al. |
| 8,142,495 B2 | 3/2012 | Hasenkam et al. |
| 8,152,821 B2 | 4/2012 | Gambale et al. |
| 8,157,810 B2 | 4/2012 | Case et al. |
| 8,167,932 B2 | 5/2012 | Bourang et al. |
| 8,167,934 B2 | 5/2012 | Styrc et al. |
| 8,187,299 B2 | 5/2012 | Goldfarb et al. |
| 8,206,439 B2 | 6/2012 | Gomez Duran |
| 8,216,301 B2 | 7/2012 | Bonhoeffer et al. |
| 8,226,711 B2 | 7/2012 | Mortier et al. |
| 8,236,045 B2 | 8/2012 | Benichou et al. |
| 8,241,274 B2 | 8/2012 | Keogh et al. |
| 8,252,051 B2 | 8/2012 | Chau et al. |
| 8,303,653 B2 | 11/2012 | Bonhoeffer et al. |
| 8,308,796 B2 | 11/2012 | Lashinski et al. |
| 8,323,334 B2 | 12/2012 | Deem et al. |
| 8,353,955 B2 | 1/2013 | Styrc et al. |
| RE44,075 E | 3/2013 | Williamson et al. |
| 8,449,599 B2 | 5/2013 | Chau et al. |
| 8,454,656 B2 | 6/2013 | Tuval |
| 8,470,028 B2 | 6/2013 | Thornton et al. |
| 8,480,730 B2 | 7/2013 | Maurer et al. |
| 8,486,138 B2 | 7/2013 | Vesely |
| 8,506,623 B2 | 8/2013 | Wilson et al. |
| 8,506,624 B2 | 8/2013 | Vidlund et al. |
| 8,578,705 B2 | 11/2013 | Sindano et al. |
| 8,579,913 B2 | 11/2013 | Nielsen |
| 8,591,573 B2 | 11/2013 | Barone |
| 8,591,576 B2 | 11/2013 | Hasenkam et al. |
| 8,597,347 B2 | 12/2013 | Maurer et al. |
| 8,685,086 B2 | 4/2014 | Navia et al. |
| 8,790,394 B2 | 7/2014 | Miller et al. |
| 8,845,717 B2 | 9/2014 | Khairkhahan et al. |
| 8,888,843 B2 | 11/2014 | Khairkhahan et al. |
| 8,900,214 B2 | 12/2014 | Nance et al. |
| 8,900,295 B2 | 12/2014 | Migliazza et al. |
| 8,926,696 B2 | 1/2015 | Cabiri et al. |
| 8,932,342 B2 | 1/2015 | McHugo et al. |
| 8,932,348 B2 | 1/2015 | Solem et al. |
| 8,945,208 B2 | 2/2015 | Jimenez et al. |
| 8,956,407 B2 | 2/2015 | Macoviak et al. |
| 8,979,922 B2 | 3/2015 | Thambar et al. |
| 8,986,376 B2 | 3/2015 | Solem |
| 9,011,522 B2 | 4/2015 | Annest et al. |
| 9,023,099 B2 | 5/2015 | Duffy et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,078,645 B2 | 7/2015 | Conklin et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,125,742 B2 | 9/2015 | Yoganathan et al. |
| 9,149,357 B2 | 10/2015 | Sequin |
| 9,161,837 B2 | 10/2015 | Kapadia |
| 9,168,137 B2 | 10/2015 | Subramanian et al. |
| 9,232,995 B2 | 1/2016 | Kovalsky et al. |
| 9,232,998 B2 | 1/2016 | Wilson et al. |
| 9,232,999 B2 | 1/2016 | Maurer et al. |
| 9,241,702 B2 | 1/2016 | Maisano et al. |
| 9,254,192 B2 | 2/2016 | Lutter et al. |
| 9,265,608 B2 | 2/2016 | Miller et al. |
| 9,289,295 B2 | 3/2016 | Aklog et al. |
| 9,289,297 B2 | 3/2016 | Wilson et al. |
| 9,345,573 B2 | 5/2016 | Nyuli et al. |
| 9,480,557 B2 | 11/2016 | Pellegrini et al. |
| 9,480,559 B2 | 11/2016 | Vidlund et al. |
| 9,526,611 B2 | 12/2016 | Tegels et al. |
| 9,597,181 B2 | 3/2017 | Christianson et al. |
| 9,610,159 B2 | 4/2017 | Christianson et al. |
| 9,675,454 B2 | 6/2017 | Vidlund et al. |
| 9,730,792 B2 | 8/2017 | Lutter et al. |
| 9,827,092 B2 | 11/2017 | Vidlund et al. |
| 9,833,315 B2 | 12/2017 | Vidlund et al. |
| 9,867,700 B2 | 1/2018 | Bakis et al. |
| 9,895,221 B2 | 2/2018 | Vidlund |
| 2001/0018611 A1 | 8/2001 | Solem et al. |
| 2001/0021872 A1 | 9/2001 | Bailey et al. |
| 2001/0025171 A1 | 9/2001 | Mortier et al. |
| 2002/0010427 A1 | 1/2002 | Scarfone et al. |
| 2002/0116054 A1 | 8/2002 | Lundell et al. |
| 2002/0139056 A1 | 10/2002 | Finnell |
| 2002/0151961 A1 | 10/2002 | Lashinski et al. |
| 2002/0161377 A1 | 10/2002 | Rabkin |
| 2002/0173842 A1 | 11/2002 | Buchanan |
| 2002/0183827 A1 | 12/2002 | Derus et al. |
| 2003/0010509 A1 | 1/2003 | Hoffman |
| 2003/0036698 A1 | 2/2003 | Kohler et al. |
| 2003/0050694 A1 | 3/2003 | Yang et al. |
| 2003/0078652 A1 | 4/2003 | Sutherland |
| 2003/0100939 A1 | 5/2003 | Yodfat et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0130731 A1 | 7/2003 | Vidlund et al. |
| 2003/0149476 A1 | 8/2003 | Damm et al. |
| 2003/0212454 A1 | 11/2003 | Scott et al. |
| 2003/0233022 A1* | 12/2003 | Vidlund ............ A61B 17/00234 600/16 |
| 2004/0039436 A1 | 2/2004 | Spenser et al. |
| 2004/0049266 A1 | 3/2004 | Anduiza et al. |
| 2004/0064014 A1 | 4/2004 | Melvin et al. |
| 2004/0092858 A1 | 5/2004 | Wilson et al. |
| 2004/0093075 A1 | 5/2004 | Kuehne |
| 2004/0097865 A1 | 5/2004 | Anderson et al. |
| 2004/0127983 A1 | 7/2004 | Mortier et al. |
| 2004/0133263 A1 | 7/2004 | Dusbabek et al. |
| 2004/0147958 A1 | 7/2004 | Lam et al. |
| 2004/0152947 A1 | 8/2004 | Schroeder et al. |
| 2004/0162610 A1 | 8/2004 | Liska et al. |
| 2004/0163828 A1 | 8/2004 | Silverstein et al. |
| 2004/0181239 A1 | 9/2004 | Dorn et al. |
| 2004/0186565 A1 | 9/2004 | Schreck |
| 2004/0186566 A1 | 9/2004 | Hindrichs et al. |
| 2004/0260317 A1 | 12/2004 | Bloom et al. |
| 2004/0260389 A1 | 12/2004 | Case et al. |
| 2005/0004652 A1 | 1/2005 | Van der Burg et al. |
| 2005/0004666 A1 | 1/2005 | Alfieri et al. |
| 2005/0075727 A1 | 4/2005 | Wheatley |
| 2005/0080402 A1 | 4/2005 | Santamore et al. |
| 2005/0085900 A1 | 4/2005 | Case et al. |
| 2005/0096498 A1 | 5/2005 | Houser et al. |
| 2005/0107661 A1 | 5/2005 | Lau et al. |
| 2005/0113798 A1 | 5/2005 | Slater et al. |
| 2005/0113810 A1 | 5/2005 | Houser et al. |
| 2005/0113811 A1 | 5/2005 | Houser et al. |
| 2005/0119519 A9 | 6/2005 | Girard et al. |
| 2005/0121206 A1 | 6/2005 | Dolan |
| 2005/0125012 A1 | 6/2005 | Houser et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0137698 A1 | 6/2005 | Salahieh et al. |
| 2005/0148815 A1 | 7/2005 | Mortier et al. |

(56) References Cited

U.S. PATENT DOCUMENTS

| | | |
|---|---|---|
| 2005/0177180 A1 | 8/2005 | Kaganov et al. |
| 2005/0197695 A1 | 9/2005 | Stacchino |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0234546 A1 | 10/2005 | Nugent et al. |
| 2005/0240200 A1 | 10/2005 | Bergheim |
| 2005/0251209 A1 | 11/2005 | Saadat et al. |
| 2005/0256567 A1 | 11/2005 | Lim et al. |
| 2005/0283231 A1 | 12/2005 | Haug et al. |
| 2005/0288766 A1 | 12/2005 | Plain et al. |
| 2006/0004442 A1 | 1/2006 | Spenser et al. |
| 2006/0025784 A1 | 2/2006 | Starksen et al. |
| 2006/0025857 A1 | 2/2006 | Bergheim et al. |
| 2006/0030885 A1 | 2/2006 | Hyde |
| 2006/0042803 A1 | 3/2006 | Gallaher |
| 2006/0047338 A1 | 3/2006 | Jenson et al. |
| 2006/0052868 A1 | 3/2006 | Mortier et al. |
| 2006/0058872 A1 | 3/2006 | Salahieh et al. |
| 2006/0094983 A1 | 5/2006 | Burbank et al. |
| 2006/0129025 A1 | 6/2006 | Levine et al. |
| 2006/0142784 A1 | 6/2006 | Kontos |
| 2006/0161040 A1 | 7/2006 | McCarthy et al. |
| 2006/0161249 A1 | 7/2006 | Realyvasquez et al. |
| 2006/0167541 A1 | 7/2006 | Lattouf |
| 2006/0195134 A1 | 8/2006 | Crittenden |
| 2006/0195183 A1 | 8/2006 | Navia et al. |
| 2006/0229708 A1 | 10/2006 | Powell et al. |
| 2006/0229719 A1 | 10/2006 | Marquez et al. |
| 2006/0241745 A1 | 10/2006 | Solem |
| 2006/0247491 A1 | 11/2006 | Vidlund et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0276874 A1 | 12/2006 | Wilson et al. |
| 2006/0282161 A1 | 12/2006 | Huynh et al. |
| 2006/0287716 A1 | 12/2006 | Banbury et al. |
| 2006/0287717 A1 | 12/2006 | Rowe et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0016286 A1 | 1/2007 | Herrmann et al. |
| 2007/0016288 A1 | 1/2007 | Gurskis et al. |
| 2007/0027535 A1 | 2/2007 | Purdy et al. |
| 2007/0038291 A1 | 2/2007 | Case et al. |
| 2007/0050020 A1 | 3/2007 | Spence |
| 2007/0061010 A1 | 3/2007 | Hauser et al. |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0083076 A1 | 4/2007 | Lichtenstein |
| 2007/0083259 A1 | 4/2007 | Bloom et al. |
| 2007/0093890 A1 | 4/2007 | Eliasen et al. |
| 2007/0100439 A1 | 5/2007 | Cangialosi et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118210 A1 | 5/2007 | Pinchuk |
| 2007/0118213 A1 | 5/2007 | Loulmet |
| 2007/0142906 A1 | 6/2007 | Figulla et al. |
| 2007/0161846 A1 | 7/2007 | Nikolic et al. |
| 2007/0162048 A1 | 7/2007 | Quinn et al. |
| 2007/0162103 A1 | 7/2007 | Case et al. |
| 2007/0168024 A1 | 7/2007 | Khairkhahan |
| 2007/0185565 A1 | 8/2007 | Schwammenthal et al. |
| 2007/0185571 A1 | 8/2007 | Kapadia et al. |
| 2007/0203575 A1 | 8/2007 | Forster et al. |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0233239 A1 | 10/2007 | Navia et al. |
| 2007/0239265 A1 | 10/2007 | Birdsall |
| 2007/0256843 A1 | 11/2007 | Pahila |
| 2007/0265609 A1 * | 11/2007 | Thapliyal .......... A61B 18/1492 606/27 |
| 2007/0265658 A1 | 11/2007 | Nelson et al. |
| 2007/0267202 A1 | 11/2007 | Mariller |
| 2007/0270932 A1 | 11/2007 | Headley et al. |
| 2007/0270943 A1 | 11/2007 | Solem |
| 2007/0293944 A1 | 12/2007 | Spenser et al. |
| 2008/0009940 A1 | 1/2008 | Cribier |
| 2008/0033543 A1 | 2/2008 | Gurskis et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082163 A1 | 4/2008 | Woo |
| 2008/0082166 A1 | 4/2008 | Styrc et al. |
| 2008/0091264 A1 | 4/2008 | Machold et al. |
| 2008/0114442 A1 | 5/2008 | Mitchell et al. |
| 2008/0125861 A1 | 5/2008 | Webler et al. |
| 2008/0147179 A1 | 6/2008 | Cai et al. |
| 2008/0154355 A1 | 6/2008 | Benichou et al. |
| 2008/0154356 A1 | 6/2008 | Obermiller et al. |
| 2008/0161911 A1 | 7/2008 | Revuelta et al. |
| 2008/0172035 A1 | 7/2008 | Starksen et al. |
| 2008/0177381 A1 | 7/2008 | Navia et al. |
| 2008/0183203 A1 | 7/2008 | Fitzgerald et al. |
| 2008/0183273 A1 | 7/2008 | Mesana et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0243150 A1 | 10/2008 | Starksen et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288060 A1 | 11/2008 | Kaye et al. |
| 2008/0293996 A1 | 11/2008 | Evans et al. |
| 2009/0005863 A1 | 1/2009 | Goetz et al. |
| 2009/0048668 A1 | 2/2009 | Wilson et al. |
| 2009/0054968 A1 | 2/2009 | Bonhoeffer et al. |
| 2009/0054974 A1 | 2/2009 | McGuckin, Jr. et al. |
| 2009/0062908 A1 | 3/2009 | Bonhoeffer et al. |
| 2009/0076598 A1 | 3/2009 | Salahieh et al. |
| 2009/0082619 A1 | 3/2009 | De Marchena |
| 2009/0088836 A1 | 4/2009 | Bishop et al. |
| 2009/0099410 A1 | 4/2009 | De Marchena |
| 2009/0112309 A1 | 4/2009 | Jaramillo |
| 2009/0131849 A1 | 5/2009 | Maurer et al. |
| 2009/0132035 A1 | 5/2009 | Roth et al. |
| 2009/0137861 A1 | 5/2009 | Goldberg et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0177266 A1 | 7/2009 | Powell et al. |
| 2009/0192601 A1 | 7/2009 | Rafiee et al. |
| 2009/0210052 A1 | 8/2009 | Forster et al. |
| 2009/0216322 A1 | 8/2009 | Le et al. |
| 2009/0222076 A1 | 9/2009 | Figulla et al. |
| 2009/0224529 A1 | 9/2009 | Gill |
| 2009/0234318 A1 | 9/2009 | Loulmet et al. |
| 2009/0234435 A1 | 9/2009 | Johnson et al. |
| 2009/0234443 A1 | 9/2009 | Ottma et al. |
| 2009/0240320 A1 | 9/2009 | Tuval et al. |
| 2009/0248149 A1 | 10/2009 | Gabbay |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0292262 A1 | 11/2009 | Adams et al. |
| 2009/0319037 A1 | 12/2009 | Rowe et al. |
| 2009/0326575 A1 | 12/2009 | Galdonik et al. |
| 2010/0016958 A1 | 1/2010 | St. Goar et al. |
| 2010/0021382 A1 | 1/2010 | Dorshow et al. |
| 2010/0023117 A1 | 1/2010 | Yoganathan et al. |

(56) References Cited

U.S. PATENT DOCUMENTS

| | | |
|---|---|---|
| 2010/0036479 A1 | 2/2010 | Hill et al. |
| 2010/0049313 A1 | 2/2010 | Alon et al. |
| 2010/0082094 A1 | 4/2010 | Quadri et al. |
| 2010/0126275 A1* | 5/2010 | Leyh ............... G01H 3/12 73/579 |
| 2010/0161041 A1 | 6/2010 | Maisano et al. |
| 2010/0168839 A1 | 7/2010 | Braido et al. |
| 2010/0179641 A1 | 7/2010 | Ryan et al. |
| 2010/0185277 A1 | 7/2010 | Braido et al. |
| 2010/0185278 A1 | 7/2010 | Schankereli |
| 2010/0191326 A1 | 7/2010 | Alkhatib |
| 2010/0192402 A1 | 8/2010 | Yamaguchi et al. |
| 2010/0204781 A1 | 8/2010 | Alkhatib |
| 2010/0210899 A1 | 8/2010 | Schankereli |
| 2010/0217382 A1 | 8/2010 | Chau et al. |
| 2010/0249489 A1 | 9/2010 | Jarvik |
| 2010/0249923 A1 | 9/2010 | Alkhatib et al. |
| 2010/0280604 A1 | 11/2010 | Zipory et al. |
| 2010/0286768 A1 | 11/2010 | Alkhatib |
| 2010/0298755 A1 | 11/2010 | McNamara et al. |
| 2010/0298931 A1 | 11/2010 | Quadri et al. |
| 2011/0004296 A1 | 1/2011 | Lutter et al. |
| 2011/0015616 A1 | 1/2011 | Straubinger et al. |
| 2011/0015728 A1 | 1/2011 | Jimenez et al. |
| 2011/0015729 A1 | 1/2011 | Jimenez et al. |
| 2011/0029072 A1 | 2/2011 | Gabbay |
| 2011/0066231 A1 | 3/2011 | Cartledge et al. |
| 2011/0066233 A1 | 3/2011 | Thornton et al. |
| 2011/0098572 A1* | 4/2011 | Chen ............... A61B 5/0062 600/463 |
| 2011/0112632 A1 | 5/2011 | Chau et al. |
| 2011/0137397 A1 | 6/2011 | Chau et al. |
| 2011/0137408 A1 | 6/2011 | Bergheim |
| 2011/0224655 A1 | 9/2011 | Asirvatham et al. |
| 2011/0224678 A1 | 9/2011 | Gabbay |
| 2011/0224728 A1 | 9/2011 | Martin et al. |
| 2011/0224784 A1 | 9/2011 | Quinn |
| 2011/0245911 A1 | 10/2011 | Quill et al. |
| 2011/0251682 A1 | 10/2011 | Murray, III et al. |
| 2011/0264191 A1 | 10/2011 | Rothstein |
| 2011/0264206 A1 | 10/2011 | Tabor |
| 2011/0288637 A1 | 11/2011 | De Marchena |
| 2011/0319988 A1 | 12/2011 | Schankereli et al. |
| 2011/0319989 A1 | 12/2011 | Lane et al. |
| 2012/0010694 A1 | 1/2012 | Lutter et al. |
| 2012/0016468 A1 | 1/2012 | Robin et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0053686 A1 | 3/2012 | McNamara et al. |
| 2012/0059487 A1 | 3/2012 | Cunanan et al. |
| 2012/0089171 A1 | 4/2012 | Hastings et al. |
| 2012/0101571 A1 | 4/2012 | Thambar et al. |
| 2012/0101572 A1 | 4/2012 | Kovalsky et al. |
| 2012/0116351 A1 | 5/2012 | Chomas et al. |
| 2012/0123529 A1 | 5/2012 | Levi et al. |
| 2012/0130391 A1* | 5/2012 | Sundt, III ............... A61M 1/10 606/108 |
| 2012/0165930 A1 | 6/2012 | Gifford et al. |
| 2012/0179244 A1 | 7/2012 | Schankereli et al. |
| 2012/0203336 A1 | 8/2012 | Annest |
| 2012/0215303 A1 | 8/2012 | Quadri et al. |
| 2012/0226348 A1 | 9/2012 | Lane et al. |
| 2012/0283824 A1 | 11/2012 | Lutter et al. |
| 2012/0289945 A1 | 11/2012 | Segermark |
| 2013/0030522 A1 | 1/2013 | Rowe et al. |
| 2013/0053950 A1 | 2/2013 | Rowe et al. |
| 2013/0066341 A1 | 3/2013 | Ketai et al. |
| 2013/0079873 A1 | 3/2013 | Migliazza et al. |
| 2013/0131788 A1 | 5/2013 | Quadri et al. |
| 2013/0172978 A1 | 7/2013 | Vidlund et al. |
| 2013/0184811 A1 | 7/2013 | Rowe et al. |
| 2013/0190860 A1 | 7/2013 | Sundt, III |
| 2013/0190861 A1 | 7/2013 | Chau et al. |
| 2013/0197622 A1 | 8/2013 | Mitra et al. |
| 2013/0226288 A1 | 8/2013 | Goldwasser et al. |
| 2013/0231735 A1 | 9/2013 | Deem et al. |
| 2013/0274874 A1 | 10/2013 | Hammer |
| 2013/0282101 A1 | 10/2013 | Eidenschink et al. |
| 2013/0310928 A1 | 11/2013 | Morriss et al. |
| 2013/0317603 A1 | 11/2013 | McLean et al. |
| 2013/0325041 A1 | 12/2013 | Annest et al. |
| 2013/0325110 A1 | 12/2013 | Khalil et al. |
| 2013/0338752 A1 | 12/2013 | Geusen et al. |
| 2014/0046433 A1 | 2/2014 | Kovalsky |
| 2014/0081323 A1 | 3/2014 | Hawkins |
| 2014/0094918 A1 | 4/2014 | Vishnubholta et al. |
| 2014/0142691 A1 | 5/2014 | Pouletty |
| 2014/0163668 A1 | 6/2014 | Rafiee |
| 2014/0194981 A1 | 7/2014 | Menk et al. |
| 2014/0194983 A1 | 7/2014 | Kovalsky et al. |
| 2014/0214159 A1 | 7/2014 | Vidlund et al. |
| 2014/0222142 A1 | 8/2014 | Kovalsky et al. |
| 2014/0243966 A1 | 8/2014 | Garde et al. |
| 2014/0277419 A1 | 9/2014 | Garde et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296972 A1 | 10/2014 | Tegels et al. |
| 2014/0296975 A1 | 10/2014 | Tegels et al. |
| 2014/0303718 A1 | 10/2014 | Tegels et al. |
| 2014/0309732 A1 | 10/2014 | Solem |
| 2014/0316516 A1 | 10/2014 | Vidlund et al. |
| 2014/0324160 A1 | 10/2014 | Benichou et al. |
| 2014/0324161 A1 | 10/2014 | Tegels et al. |
| 2014/0324164 A1 | 10/2014 | Gross et al. |
| 2014/0331475 A1 | 11/2014 | Duffy et al. |
| 2014/0358224 A1 | 12/2014 | Tegels et al. |
| 2014/0364942 A1 | 12/2014 | Straubinger et al. |
| 2014/0364944 A1 | 12/2014 | Lutter et al. |
| 2014/0379076 A1 | 12/2014 | Vidlund et al. |
| 2015/0005874 A1 | 1/2015 | Vidlund et al. |
| 2015/0011821 A1 | 1/2015 | Gorman et al. |
| 2015/0025553 A1 | 1/2015 | Del Nido et al. |
| 2015/0057705 A1 | 2/2015 | Vidlund et al. |
| 2015/0073542 A1 | 3/2015 | Heldman |
| 2015/0073545 A1 | 3/2015 | Braido |
| 2015/0094802 A1 | 4/2015 | Buchbinder et al. |
| 2015/0105856 A1 | 4/2015 | Rowe et al. |
| 2015/0119936 A1 | 4/2015 | Gilmore et al. |
| 2015/0119978 A1 | 4/2015 | Tegels et al. |
| 2015/0127093 A1 | 5/2015 | Hosmer et al. |
| 2015/0127096 A1 | 5/2015 | Rowe et al. |
| 2015/0134050 A1 | 5/2015 | Solem et al. |
| 2015/0142100 A1 | 5/2015 | Morriss et al. |
| 2015/0142101 A1 | 5/2015 | Coleman et al. |
| 2015/0142103 A1 | 5/2015 | Vidlund |
| 2015/0142104 A1 | 5/2015 | Braido |
| 2015/0173897 A1 | 6/2015 | Raanani et al. |
| 2015/0196393 A1 | 7/2015 | Vidlund et al. |
| 2015/0196688 A1 | 7/2015 | James et al. |
| 2015/0202044 A1 | 7/2015 | Chau et al. |
| 2015/0216653 A1 | 8/2015 | Freudenthanl |
| 2015/0216660 A1 | 8/2015 | Pintor et al. |
| 2015/0223820 A1 | 8/2015 | Olson et al. |
| 2015/0223934 A1 | 8/2015 | Vidlund et al. |
| 2015/0238312 A1 | 8/2015 | Lashinski |
| 2015/0238729 A1 | 8/2015 | Jenson et al. |
| 2015/0272731 A1 | 10/2015 | Racchini et al. |
| 2015/0305860 A1 | 10/2015 | Wang et al. |
| 2015/0305864 A1 | 10/2015 | Quadri et al. |
| 2015/0305868 A1 | 10/2015 | Lutter et al. |
| 2015/0327995 A1 | 11/2015 | Morin et al. |
| 2015/0328001 A1 | 11/2015 | McLean et al. |
| 2015/0335424 A1 | 11/2015 | McLean et al. |
| 2015/0335429 A1 | 11/2015 | Morriss et al. |
| 2015/0342717 A1 | 12/2015 | O'Donnell et al. |
| 2015/0351903 A1 | 12/2015 | Morriss et al. |
| 2015/0351906 A1 | 12/2015 | Hammer et al. |
| 2016/0000562 A1 | 1/2016 | Siegel |
| 2016/0008131 A1 | 1/2016 | Christianson et al. |
| 2016/0067042 A1 | 3/2016 | Murad et al. |
| 2016/0074160 A1 | 3/2016 | Christianson et al. |

(56) References Cited

U.S. PATENT DOCUMENTS

| | | |
|---|---|---|
| 2016/0106537 A1 | 4/2016 | Christianson et al. |
| 2016/0113764 A1 | 4/2016 | Sheahan et al. |
| 2016/0143736 A1 | 5/2016 | Vidlund et al. |
| 2016/0151155 A1 | 6/2016 | Lutter et al. |
| 2016/0242902 A1 | 8/2016 | Morriss et al. |
| 2016/0262879 A1 | 9/2016 | Meiri et al. |
| 2016/0262881 A1 | 9/2016 | Schankereli et al. |
| 2016/0278955 A1 | 9/2016 | Liu et al. |
| 2016/0317290 A1 | 11/2016 | Chau et al. |
| 2016/0324635 A1 | 11/2016 | Vidlund et al. |
| 2016/0331527 A1 | 11/2016 | Vidlund et al. |
| 2016/0346086 A1 | 12/2016 | Solem |
| 2016/0367365 A1 | 12/2016 | Conklin |
| 2016/0367367 A1 | 12/2016 | Maisano et al. |
| 2016/0367368 A1 | 12/2016 | Vidlund et al. |
| 2017/0079790 A1 | 3/2017 | Vidlund et al. |
| 2017/0100248 A1 | 4/2017 | Tegels et al. |
| 2017/0128208 A1 | 5/2017 | Christianson et al. |
| 2017/0181854 A1 | 6/2017 | Christianson et al. |
| 2017/0196688 A1 | 7/2017 | Christianson et al. |
| 2017/0252153 A1 | 9/2017 | Chau et al. |
| 2017/0266001 A1 | 9/2017 | Vidlund et al. |
| 2017/0281343 A1 | 10/2017 | Christianson et al. |
| 2017/0312076 A1 | 11/2017 | Lutter et al. |
| 2017/0312077 A1 | 11/2017 | Vidlund et al. |
| 2017/0319333 A1 | 11/2017 | Tegels et al. |
| 2018/0028314 A1 | 2/2018 | Ekvall et al. |
| 2018/0078368 A1 | 3/2018 | Vidlund et al. |
| 2018/0078370 A1 | 3/2018 | Kovalsky et al. |

FOREIGN PATENT DOCUMENTS

| | | |
|---|---|---|
| CN | 2902226 | 5/2007 |
| CN | 101146484 | 3/2008 |
| CN | 101180010 | 5/2008 |
| CN | 101984938 | 3/2011 |
| CN | 102869317 | 1/2013 |
| CN | 102869318 | 1/2013 |
| CN | 102869321 | 1/2013 |
| CN | 103220993 | 7/2013 |
| CN | 102639179 B | 10/2014 |
| DE | 2246526 | 3/1973 |
| DE | 19532846 | 3/1997 |
| DE | 19546692 | 6/1997 |
| DE | 19857887 | 7/2000 |
| DE | 19907646 | 8/2000 |
| DE | 10049812 | 4/2002 |
| DE | 10049813 | 4/2002 |
| DE | 10049815 | 4/2002 |
| DE | 102006052564 | 12/2007 |
| DE | 102006052710 | 5/2008 |
| DE | 102007043830 A1 | 4/2009 |
| DE | 102007043831 | 4/2009 |
| EP | 0103546 | 5/1988 |
| EP | 1057460 | 12/2000 |
| EP | 1088529 | 4/2001 |
| EP | 1469797 | 11/2005 |
| EP | 2111800 | 10/2009 |
| EP | 2193762 | 6/2010 |
| EP | 2747707 | 4/2015 |
| EP | 2918248 | 9/2015 |
| EP | 2278944 | 3/2016 |
| FR | 2788217 | 7/2000 |
| FR | 2815844 | 5/2002 |
| JP | 2003-505146 | 2/2003 |
| JP | 2005-515836 | 6/2005 |
| JP | 2009-514628 | 4/2009 |
| JP | 2013-512765 | 4/2013 |
| NL | 1017275 | 8/2002 |
| SU | 1271508 | 11/1986 |
| WO | WO 92/17118 | 10/1992 |
| WO | WO 93/01768 | 2/1993 |
| WO | WO 98/29057 | 7/1998 |
| WO | WO 99/40964 | 8/1999 |
| WO | WO 99/47075 | 9/1999 |
| WO | WO 2000/018333 | 4/2000 |
| WO | WO 2000/030550 | 6/2000 |
| WO | WO 2000/041652 | 7/2000 |
| WO | WO 2000/047139 | 8/2000 |
| WO | WO 2001/035878 | 5/2001 |
| WO | WO 2001/049213 | 7/2001 |
| WO | WO 2001/054624 | 8/2001 |
| WO | WO 2001/054625 | 8/2001 |
| WO | WO 2001/056512 | 8/2001 |
| WO | WO 2001/061289 | 8/2001 |
| WO | WO 2001/076510 | 10/2001 |
| WO | WO 2001/082840 | 11/2001 |
| WO | WO 2002/004757 | 1/2002 |
| WO | WO 2002/022054 | 3/2002 |
| WO | WO 2002/028321 | 4/2002 |
| WO | WO 2002/036048 | 5/2002 |
| WO | WO 2002/041789 | 5/2002 |
| WO | WO 2002/043620 | 6/2002 |
| WO | WO 2002/049540 | 6/2002 |
| WO | WO 2002/076348 | 10/2002 |
| WO | WO 2003/003943 | 1/2003 |
| WO | WO 2003/030776 | 4/2003 |
| WO | WO 2003/047468 | 6/2003 |
| WO | WO 2003/049619 | 6/2003 |
| WO | WO 2004/019825 | 3/2004 |
| WO | WO 2005/102181 | 11/2005 |
| WO | WO 2006/014233 | 2/2006 |
| WO | WO 2006/034008 | 3/2006 |
| WO | WO 2006/064490 | 6/2006 |
| WO | WO 2006/070372 | 7/2006 |
| WO | WO 2006/113906 | 10/2006 |
| WO | WO 2006/127756 | 11/2006 |
| WO | WO 2007/081412 | 7/2007 |
| WO | WO 2008/005405 | 1/2008 |
| WO | WO 2008/035337 | 3/2008 |
| WO | WO 2008/091515 | 7/2008 |
| WO | WO 2008/125906 | 10/2008 |
| WO | WO 2008/147964 | 12/2008 |
| WO | WO 2009/024859 | 2/2009 |
| WO | WO 2009/026563 | 2/2009 |
| WO | WO 2009/045338 | 4/2009 |
| WO | WO 2009/132187 | 10/2009 |
| WO | WO 2010/090878 | 8/2010 |
| WO | WO 2010/098857 | 9/2010 |
| WO | WO 2010/121076 | 10/2010 |
| WO | WO 2011/017440 | 2/2011 |
| WO | WO 2011/022658 | 2/2011 |
| WO | WO 2011/069048 | 6/2011 |
| WO | WO 2011/072084 | 6/2011 |
| WO | WO 2011/106735 | 9/2011 |
| WO | WO 2011/109813 | 9/2011 |
| WO | WO 2011/159342 | 12/2011 |
| WO | WO 2011/163275 | 12/2011 |
| WO | WO 2012/027487 | 3/2012 |
| WO | WO 2012/036742 | 3/2012 |
| WO | WO 2012/095116 | 7/2012 |
| WO | WO 2012/177942 | 12/2012 |
| WO | WO 2013/045262 | 4/2013 |
| WO | WO 2013/059747 | 4/2013 |
| WO | WO 2013/096411 | 6/2013 |
| WO | WO 2013/175468 | 11/2013 |
| WO | WO 2014/121280 | 8/2014 |
| WO | WO 2014/144937 | 9/2014 |
| WO | WO 2014/162306 | 10/2014 |
| WO | WO 2014/189974 | 11/2014 |
| WO | WO 2015/051430 | 4/2015 |
| WO | WO 2015/058039 | 4/2015 |
| WO | WO 2015/063580 | 5/2015 |
| WO | WO 2015/065646 | 5/2015 |
| WO | WO 2015/120122 | 8/2015 |
| WO | WO 2015/138306 | 9/2015 |
| WO | WO 2015/173609 | 11/2015 |
| WO | WO 2016/112085 | 7/2016 |
| WO | WO 2016/126942 | 8/2016 |
| WO | WO 2016/168609 | 10/2016 |
| WO | WO 2016/196933 | 12/2016 |
| WO | WO 2017/096157 | 6/2017 |
| WO | WO 2017/132008 | 8/2017 |

(56) References Cited

FOREIGN PATENT DOCUMENTS

| WO | WO 2017/218375 | 12/2017 |
|---|---|---|
| WO | WO 2018/005779 | 1/2018 |
| WO | WO 2018/013515 | 1/2018 |

OTHER PUBLICATIONS

International Search Report and Written Opinion for International Application No. PCT/US2014/061046, dated Feb. 24, 2015, 13 pages.
Al Zaibag, M. et al., "Percutaneous Balloon Valvotomy in Tricuspid Stenosis," British Heart Journal, Jan. 1987, 57(1):51-53.
Al-Khaja, N. et al., "Eleven Years' Experience with Carpentier-Edwards Biological Valves in Relation to Survival and Complications," European Journal of Cardiothoracic Surgery, Jun. 30, 1989, 3:305-311.
Almagor, Y. et al., "Balloon Expandable Stent Implantation in Stenotic Right Heart Valved Conduits," Journal of the American College of Cardiology, Nov. 1, 1990, 16(6):1310-1314.
Andersen, H. R. et al., "Transluminal implantation of artificial heart valves. Description of a new expandable aortic valve and initial results with implantation by catheter technique in closed chest pigs," European Heart Journal, 1992, 13(5):704-708.
Andersen, H. R., "History of Percutaneous Aortic Valve Prosthesis," Herz, Aug. 2009, 34(5):343-346.
Andersen, H. R., "Transluminal catheter implanted prosthetic heart valves," International Journal of Angiology, 1998, 7(2):102-106.
Ashton, R. C., Jr. et al., "Development of an Intraluminal Device for the Treatment of Aortic Regurgitation: Prototype and in Vitro Testing System," Journal of Thoracic and Cardiovascular Surgery, 1996, 112:979-983.
Benchimol, A. et al., "Simultaneous Left Ventricular Echocardiography and Aortic Blood Velocity During Rapid Right Ventricular Pacing in Man," The American Journal of the Medical Sciences, Jan.-Feb. 1977, 273(1):55-62.
Bernacca, G. M. et al., "Polyurethane heart valves: Fatigue failure, calcification, and polyurethane structure," Journal of Biomedical Materials Research, Mar. 5, 1997, 34(3):371-379.
Boudjemline, Y. et al., "Steps Toward the Percutaneous Replacement of Atrioventricular Valves: An Experimental Study," Journal of the American College of Cardiology, Jul. 2005, 46(2):360-365.
Buckberg, G. et al., "Restoring Papillary Muscle Dimensions During Restoration in Dilated Hearts," Interactive CardioVascular and Thoracic Surgery, 2005, 4:475-477.
Chamberlain, G., "Ceramics Replace Body Parts," Design News, Jun. 9, 1997, Issue 11, vol. 52, 5 pages.
Choo, S. J. et al., "Aortic Root Geometry: Pattern of Differences Between Leaflets and Sinuses of Valsava," The Journal of Heart Valve Disease, Jul. 1999, 8:407-415.
Declaration of Malcolm J. R. Dalrymple-Hay, Nov. 9, 2012, pp. 1-11; with Curriculum Vitae, Oct. 4, 2012.
Dotter, C. T. et al., "Transluminal Treatment of Arteriosclerotic Obstruction. Description of a New Technic and a Preliminary Report of its Application," Circulation, Nov. 1964, 30:654-670.
Drawbaugh, K., "Feature—Heart Surgeons Explore Minimally Invasive Methods," Reuters Limited, Jul. 16, 1996, 3 pages.
Gray, H., The Aorta, Anatomy of the Human Body, 1918, Retrieved from the Internet <http://www.bartleby.com/107/142.html>, Dec. 10, 2012, 5 pages.
Gray, H., The Heart, Anatomy of the Human Body, 1918, Retrieved from the Internet <http://education.yahoo.com/reference/gray/subjects/subject/138>, Aug. 10, 2012, 9 pages.
Greenhalgh, E. S., "Design and characterization of a biomimetic prosthetic aortic heart valve," 1994, ProQuest Dissertations and Theses, Department of Fiber and Polymer Science, North Carolina State University at Raleigh, 159 pages.
Inoue, K. et al., "Clinical Application of Transvenous Mitral Commissurotomy by a New Balloon Catheter," The Journal of Thoracic and Cardiovascular Surgery, 1984, 87:394-402.

Jin, X. Y. et al., "Aortic Root Geometry and Stentless Porcine Valve Competence," Seminars in Thoracic and Cardiovascular Surgery, Oct. 1999, 11(4):145-150.
Knudsen, L. L. et al., "Catheter-implanted prosthetic heart valves. Transluminal catheter implantation of a new expandable artificial heart valve in the descending thoracic aorta in isolated vessels and closed chest pigs," The International Journal of Artificial Organs, 1993, 16(5):253-262.
Kolata, G., "Device That Opens Clogged Arteries Gets a Failing Grade in a New Study," New York Times [online], <http://www.nytimes.com/1991/01/03/health/device-that-opens-clogged-arteries-gets-a-faili . . . ,>, published Jan. 3, 1991, retrieved from the Internet on Feb. 5, 2016, 3 pages.
Lawrence, D. D., "Percutaneous Endovascular Graft: Experimental Evaluation," Radiology, 1987, 163:357-360.
Lozonschi, L., et al. "Transapical mitral valved stent implantation: A survival series in swine," The Journal of Thoracic and Cardiovascular Surgery, 140(2):422-426 (Aug. 2010) published online Mar. 12, 2010, 1 page.
Lutter, G. et al., "Mitral Valved Stent Implantation," European Journal of Cardio-Thoracic Surgery, 2010, 38:350-355, 2 pages.
Ma, L. et al., "Double-crowned valved stents for off-pump mitral valve replacement," European Journal of Cardio-Thoracic Surgery, Aug. 2005, 28(2):194-198.
Moazami, N. et al., "Transluminal aortic valve placement: A feasibility study with a newly designed collapsible aortic valve," ASAIO Journal, Sep./ Oct. 1996, 42(5):M381-M385.
Orton, C., "Mitralseal: Hybrid Transcatheter Mitral Valve Replacement," Retrieved from the Internet: <http:/www.acvs.org/symposium/proceedings2011/data/papers/102.pdf>, pp. 311-312.
Pavcnik, D. et al. "Development and Initial Experimental Evaluation of a Prosthetic Aortic Valve for Transcatheter Placement," Radiology, 1992; 183:151-154.
Porstmann, W. et al., "Der Verschluβ des Ductus Arteriosus Persistens ohne Thorakotomie," Thoraxchirurgie Vaskuläre Chirurgie, Band 15, Heft 2, Stuttgart, Apr. 1967, pp. 199-203.
Rashkind, W. J., "Creation of an Atrial Septal Defect Without Thoracotomy," The Journal of the American Medical Association, Jun. 13, 1966, 196(11):173-174.
Rashkind, W. J., "Historical Aspects of Interventional Cardiology: Past, Present, Future," Texas Heart Institute Journal, Dec. 1986, 13(4):363-367.
Reul, H. et al., "The Geometry of the Aortic Root in Health, at Valve Disease and After Valve Replacement," J. Biomechanics, 1990, 23(2):181-191.
Rosch, J. et al., "The Birth, Early Years and Future of Interventional Radiology," J Vasc Interv Radiol., Jul. 2003, 4:841-853.
Ross, D. N., "Aortic Valve Surgery," Guy's Hospital, London, 1968, pp. 192-197.
Rousseau, E. P. M. et al., "A mechanical analysis of the closed Hancock heart valve prosthesis," Journal of Biomechanics, 1988, 21(7):545-562.
Sabbah, A. N. et al., "Mechanical Factors in the Degeneration of Porcine Bioprosthetic Valves: An Overview," Dec. 1989, Journal of Cardiac Surgery, 4(4):302-309.
Selby, J. B., "Experience with New Retrieval Forceps for Foreign Body Removal in the Vascular, Urinary, and Biliary Systems," Radiology, 1990, 176:535-538.
Serruys, P. W. et al., "Stenting of Coronary Arteries. Are we the Sorcerer's Apprentice?," European Heart Journal, Sep. 1989, 10(9):774-782.
"Shape Memory Alloys," Retrieved from the Internet: <http://webdocs.cs.ualberta.ca/~database/MEMS/sma.html>, Feb. 5, 2016, 3 pages.
Sigwart, U., "An Overview of Intravascular Stents: Old and New," Chapter 48, Interventional Cardiology, 2nd Edition, W.B. Saunders Company, Philadelphia, PA, © 1994, 1990, pp. 803-815.
Tofeig, M. et al., "Transcatheter Closure of a Mid-Muscular Ventricular Septal Defect with an Amplatzer VSD Occluder Device," Heart, 1999, 81:438-440.
Uchida, B. T. et al., "Modifications of Gianturco Expandable Wire Stents," Am. J. Roentgenol., May 1988, 150(5):1185-1187.

(56) References Cited

OTHER PUBLICATIONS

Watt, A. H. et al., "Intravenous Adenosine in the Treatment of the Supraventricular Tachycardia; a Dose-Ranging Study and Interaction with Dipyridamole," British Journal of Clinical Pharmacology, 1986, 21:227-230.

Webb, J. G. et al., "Percutaneous Aortic Valve Implantation Retrograde from the Femoral Artery," Circulation, 2006, 113:842-850.

Wheatley, D. J., "Valve Prostheses," Rob & Smith's Operative Surgery, Fourth Edition, 1986, pp. 415-424, Butterworths.

Yoganathan, A. P. et al., "The Current Status of Prosthetic Heart Valves," In Polymetric Materials and Artificial Organs, American Chemical Society, 1984, pp. 111-150.

\* cited by examiner

APPARATUS AND METHODS FOR ALIGNMENT AND DEPLOYMENT OF INTRACARDIAC DEVICES

CROSS-REFERENCE TO RELATED APPLICATIONS

This application is a continuation under 35 USC Section 120 of International Application No. PCT/US2014/061046, filed Oct. 17, 2014, entitled "Apparatus and Methods for Alignment and Deployment of Intracardiac Devices," which claims priority to and the benefit of U.S. Provisional Patent Application No. 61/892,390, filed Oct. 17, 2013, entitled "Apical ICE Echo Probe," each of the disclosures of which is incorporated herein by reference in its entirety.

BACKGROUND

Embodiments are described herein that relate to devices and methods for use in the deployment and alignment of a medical device such as an intracardiac device.

When deploying a prosthetic mitral valve, it is important that the valve is seated within the native annulus (for valves that do not require excision of the native valve) in such a manner as to avoid hemodynamic leakage. Leaking can occur where the prosthetic valve meets the commissures, meets the anterior leaflets, and/or meets the posterior leaflets. Accordingly, some newer generation valves are equipped with a flange or cuff that is atrially seated, maintains patency during its lifetime, and funnels cardiac atrial output through a one-way valve and into the ventricle. Accordingly, proper alignment of the annular seal is critical to the effectiveness of the valve and to the life of the patient. Thus, devices for aligning the transventricular tether of such a valve would be considered useful to solve these and other problems known in the art.

SUMMARY

Apparatus and methods are described herein for use in the alignment and deployment of a transcatheter prosthetic valve, such as a prosthetic mitral valve. In some embodiments, an apparatus includes an outer tube member defining a lumen and a needle assembly configured to be received through the lumen of the outer tube member. The needle assembly includes an elongate needle having a distal tip configured to be inserted through the epicardial surface of a heart and extend within the left ventricle of the heart. An imaging probe is coupled to the needle assembly and includes a cable and an imaging element disposed at a distal end portion of the cable. The imaging probe is configured to provide image data associated with a location of a commissural-commissural (C-C) plane and a location of the anterior-posterior (A-P) plane of the mitral valve and the annular region of the heart such that a prosthetic mitral valve can be positioned within the heart based at least in part on the C-C plane and the A-P plane.

DETAILED DESCRIPTION

Figure 1:
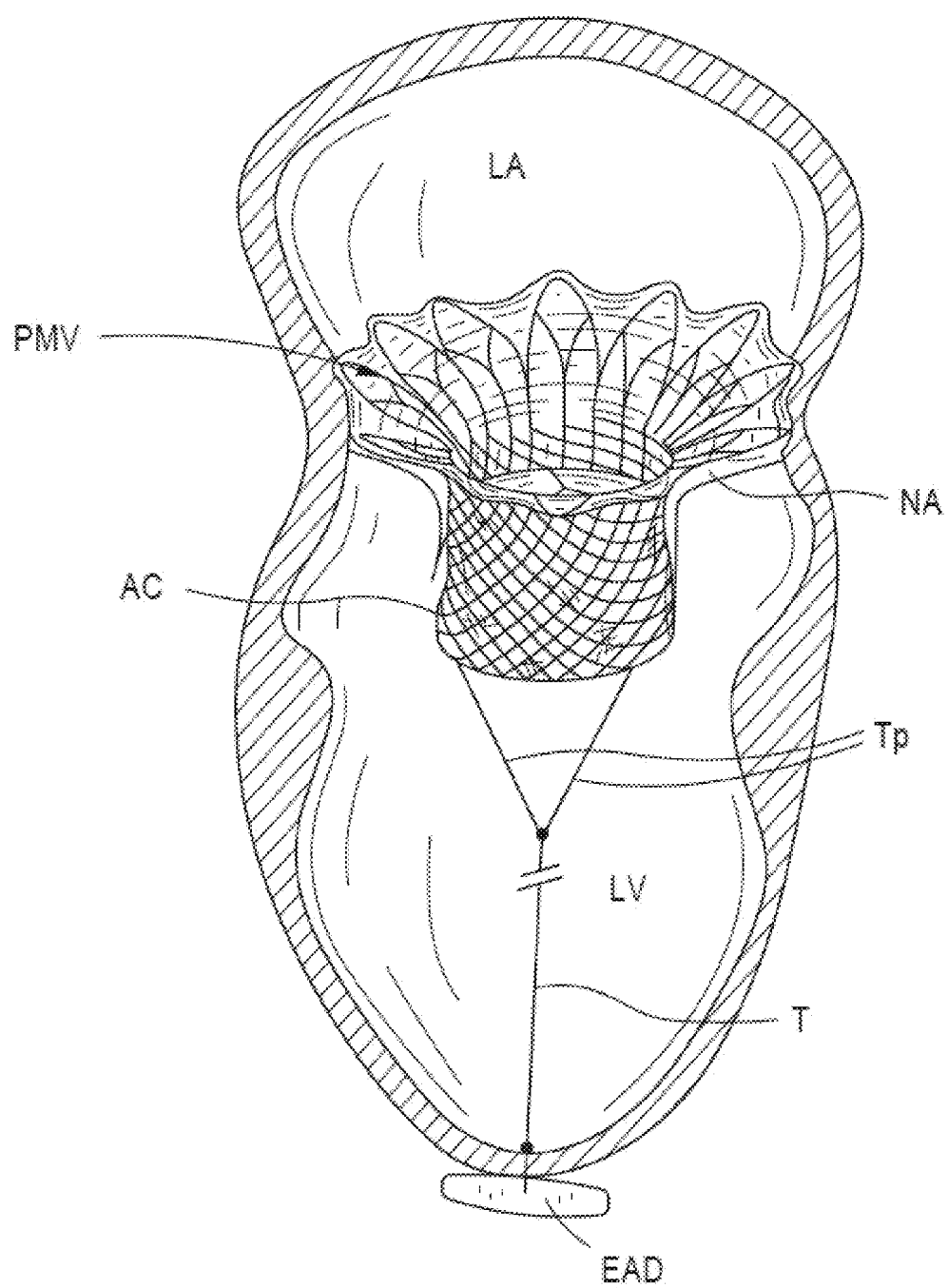
FIG. 1 is a cross-sectional illustration of portion of a heart with a prosthetic mitral valve implanted therein and an epicardial anchor device anchoring the mitral valve in position.

Apparatus and methods are described herein for use in the alignment and deployment of a transcatheter prosthetic valve, such as a prosthetic mitral valve. As described herein, an alignment device that includes an imaging probe can be used to determine a location and orientation for positioning a tether coupled to a prosthetic mitral valve and securing the tether with an epicardial pad at the epicardial surface of a heart.

In some embodiments, an alignment device includes a handheld intracardiac echocardiography (ICE) probe coupled to a percutaneous transmyocardial needle/tube component. The ICE probe can include a control wand connected to an imaging element with a cable. The imaging element includes a side-looking multi-element phased array transducer with multi-way steerability. The imaging probe can include a distal targeting loop for epicardial surface contact. The distal targeting loop can define an aperture and the percutaneous transmyocardial needle/tube component can be configured to travel along a longitudinal axis through the aperture. The alignment device is configured to facilitate alignment of the longitudinal axis of the percutaneous transmyocardial needle/tube component.

In some embodiments, the imaging probe is an 8 or 10 French probe. In some embodiments, the imaging element (e.g., transducer) can operate at a frequency ranging from about 5.0 to about 8.5 MHz. In some embodiments, the imaging probe is configured to provide greyscale imaging, color Doppler imaging, tissue imaging, and/or 3D localization.

In some embodiments, a method for aligning a prosthetic heart valve for deployment within a native mitral valve can include using an alignment device as described herein to identify the commissural-commissural (C-C) plane or axis and the anterior-posterior (A-P) plane or axis of the mitral valve and annular region. In some embodiments, the method can further include deploying an asymmetric compressed self-expanding transcatheter valve to the mitral annulus. The method further can further include orienting the asymmetric compressed self-expanding transcatheter valve to minimize left ventricular outflow tract (LVOT) obstruction.

In some embodiments, a surgical kit can include an alignment device as described herein and a transcatheter prosthetic valve delivery device both disposed within a sterile package. In some embodiments, a kit can further include a transcatheter valve (e.g., a prosthetic mitral valve) and/or an epicardial pad that can be used to secure the transcatheter valve in position within the heart.

As used herein, the words "proximal" and "distal" refer to a direction closer to and away from, respectively, an operator of, for example, a medical device. Thus, for example, the end of the medical device closest to the patient's body (e.g., contacting the patient's body or disposed within the patient's body) would be the distal end of the medical device, while the end opposite the distal end and closest to, for example, the user (or hand of the user) of the medical device, would be the proximal end of the medical device.

In some embodiments, an alignment device is described herein that can be used in conjunction with a procedure to deliver and anchor a compressible prosthetic heart valve replacement (e.g., a prosthetic mitral valve), which can be deployed into a closed beating heart using a transcatheter delivery system. An epicardial pad device or system can be used to anchor such a prosthetic heart valve replacement. Such an epicardial pad system can be deployed via a minimally invasive procedure such as, for example, a procedure utilizing the intercostal or subxyphoid space for valve introduction. In such a procedure, the prosthetic valve can be formed in such a manner that it can be compressed to fit within a delivery system and secondarily ejected from the delivery system into the target location, for example, the mitral or tricuspid valve annulus.

A compressible prosthetic mitral valve can have a shape, for example that features a tubular stent body that contains leaflets and an atrial cuff. This allows the valve to seat within the native mitral annulus. The use of a flexible valve attached using an apical tether can provide compliance with the motion and geometry of the heart. The geometry and motion of the heart are well-known as exhibiting a complicated biphasic left ventricular deformation with muscle thickening and a sequential twisting motion. The additional use of the apically secured ventricular tether helps maintain the prosthetic valve's annular position without allowing the valve to migrate, while providing enough tension between the cuff and the atrial trabeculations to reduce, and preferably eliminate, perivalvular leaking. The use of a compliant valve prosthesis and the special shape and features can help reduce or eliminate clotting and hemodynamic issues, including left ventricular outflow tract (LVOT) interference problems. Many known valves are not able to address problems with blood flow and aorta/aortic valve compression issues.

Structurally, the prosthetic heart valve can include, for example, a self-expanding tubular frame having a cuff at one end (the atrial end), one or more attachment points to which one or more tethers can be attached, preferably at or near the ventricular end of the valve, and a leaflet assembly that contains the valve leaflets, which can be formed from stabilized tissue or other suitable biological or synthetic material. In one embodiment, the leaflet assembly may include a wire form where a formed wire structure is used in conjunction with stabilized tissue to create a leaflet support structure, which can have anywhere from 1, 2, 3 or 4 leaflets, or valve cusps disposed therein. In another embodiment, the leaflet assembly can be wireless and use only the stabilized tissue and stent body to provide the leaflet support structure, and which can also have anywhere from 1, 2, 3 or 4 leaflets, or valve cusps disposed therein.

The upper cuff portion may be formed by heat-forming a portion of a tubular nitinol structure (formed from, for example, braided wire or a laser-cut tube) such that the lower portion retains the tubular shape but the upper portion is opened out of the tubular shape and expanded to create a widened collar structure that may be shaped in a variety of functional regular or irregular funnel-like or collar-like shapes.

A prosthetic mitral valve can be anchored to the heart at a location external to the heart via one or more tethers coupled to an anchor device, as described herein. For example, the tether(s) can be coupled to the prosthetic mitral valve and extend out of the heart and be secured at an exterior location (e.g., the epicardial surface) with an anchor device, as described herein. An anchor device can be used with one or more such tethers in other surgical situations where such a tether may be desired to extend from an intraluminal cavity to an external anchoring site.

FIG. 1 is a cross-sectional illustration of the left ventricle LV and left atrium LA of a heart having a transcatheter prosthetic mitral valve PMV deployed therein and an epicardial anchor device EAD securing the prosthetic mitral valve PMV in place. FIG. 1 illustrates the prosthetic mitral valve PMV seated into the native valve annulus NA and held there using an atrial cuff AC of the prosthetic mitral valve PMV, the radial tension from the native leaflets, and a ventricular tether T secured with attachment portions Tp to the prosthetic mitral valve PMV and to the epicardial anchor EAD. The apparatus and methods described herein can be used in conjunction with the various different types and embodiments of an epicardial anchor device, such as those described in pending International Patent Application No. PCT/2014/049218 entitled "Epicardial Anchor Devices and Methods," ("PCT application '049218") the disclosure of which is incorporated herein by reference in its entirety.

Figure 2A:
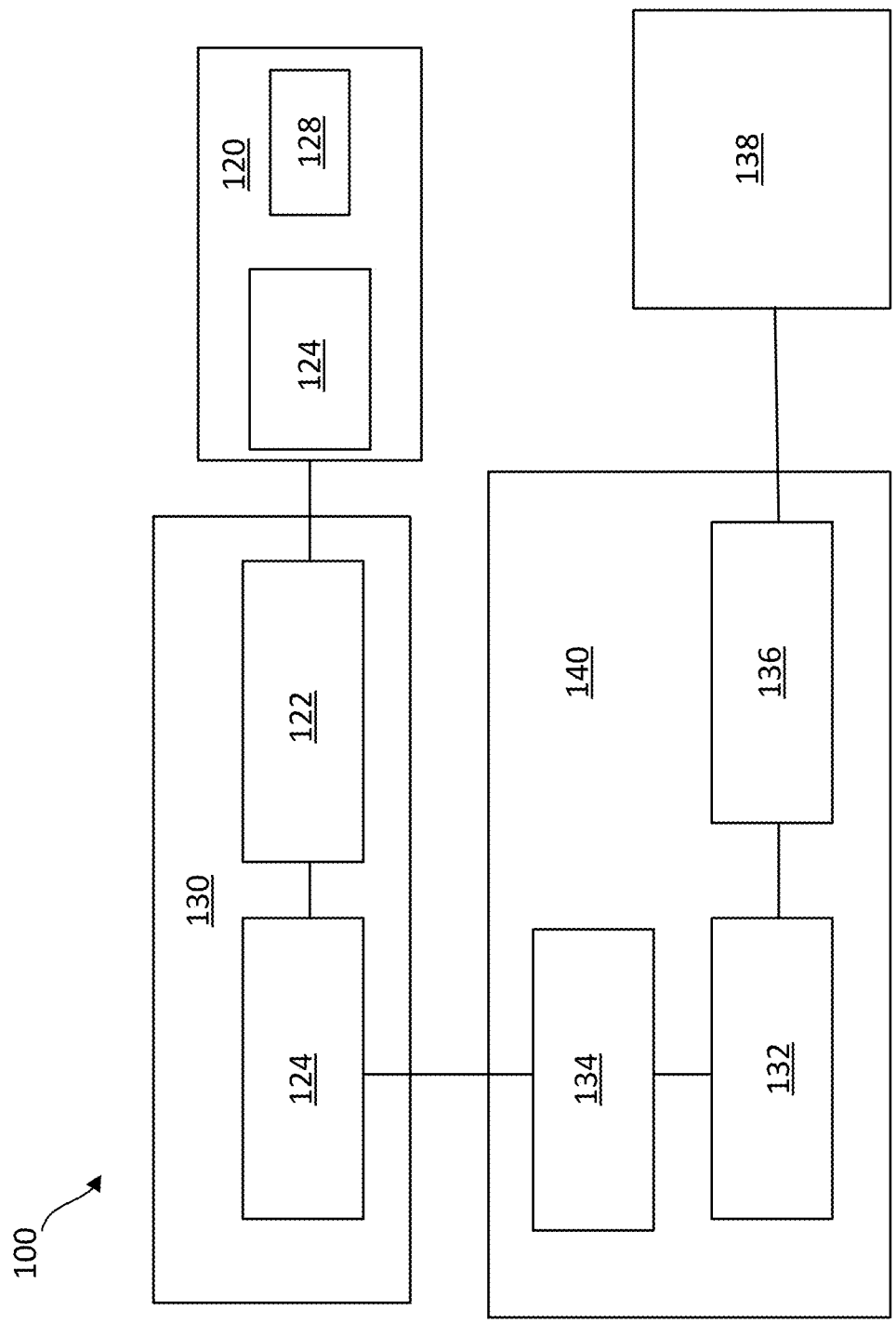
FIG. 2A is a schematic illustration of an alignment device, according to an embodiment.

FIG. 2A is a schematic illustration of an alignment device, according to an embodiment. An alignment device 100 includes a needle assembly 120, a tube assembly 130 and an imaging probe 140. The tube assembly 130 includes an outer tube member 122 and an imaging element coupling member 124 coupled to a distal end portion of the outer tube member 122. The needle assembly 120 is movably received at least partially within a lumen defined by the outer tube member 122. The needle assembly 120 includes a needle tube 126 and an elongate needle 128 that is at least partially movably received through a lumen of the needle tube 126. The elongate needle 128 includes a distal tip or stylet 129 (shown in FIG. 2B) configured to pierce through tissue.

The imaging probe 140 is coupled to the outer tube member 122 and/or the imaging element coupling member 124. The imaging probe 140 includes an elongate cable 132 coupled on a proximal end to a handle assembly 136 and having on a distal end portion an imaging component 134. The distal end portion and imaging element 134 can be coupled to the imaging element coupling member 124 of the tube assembly 130. The cable 132 electrically and operatively couples the imaging element 134 to control components (not shown) included in the handle 136. In some embodiments, the imaging probe 140 can be, for example, an 8 or 10 French Acuson AcuNav™ device that is coupled to the outer tube member 122. The imaging element 134 can include one or more ultrasound transducers. In some embodiments, the imaging element 134 can include a side-looking 64-element phased array transducer with 4-way steerability, can operate at a frequency ranging from about 5.0-8.5 MHz or about 5.0-7.0 MHz, and/or provide grey-scale imaging, color doppler imaging, tissue imaging, and/or 3D localization with Cartosound. In other embodiments, the imaging probe can be, for example, a known probe such as the UltraICE device from Boston Scientific, the EP Med View Flex catheter or ClearICE from St. Jude Medical, or the SoundStar from Biosense-Webster, or functionally similar to any one of these example imaging devices. Such a known imaging probe can be coupled to the tube assembly 130 as described above.

The handle 136 can be operatively coupleable to a computer device 138 that includes, for example, a display device (e.g., a computer monitor) such that image data collected by the imaging element 134 can be collected and stored within a memory of the computer device 138 and can be viewed on the display device. In some embodiments, an additional sleeve member (not shown in FIG. 2) is also included. In such an embodiment, a portion of the cable 132 and a portion of the outer tube member 122 can be received within a lumen of the sleeve member as described and shown with reference to the embodiment illustrated in FIGS. 3 and 4.

The alignment device 100 can be used in conjunction with a prosthetic intracardiac delivery device to facilitate the alignment and positioning of an intracardiac device such as, for example, a prosthetic mitral valve. The alignment device 100 can be used to determine a desired or optimal location on the epicardial surface to place an epicardial pad to secure a tether attached to a prosthetic valve as described in more detail below. The alignment device 100 can also be used to provide image data of the heart such that the commissural-commissural (C-C) plane or axis and the apical-posterior (A-P) plane or axis of the mitral valve and the annular region of the heart can be identified. This information can then be used to position and align a prosthetic mitral device in a desired location and orientation as described in more detail below with reference to specific embodiments. Thus, during a procedure, after using the alignment device 100, a prosthetic mitral valve can be deployed within the left atrium of the heart and a tether coupled to the prosthetic mitral valve and extending outside the heart can be aligned and secured at a desired location with an epicardial pad device.

Figure 2B:
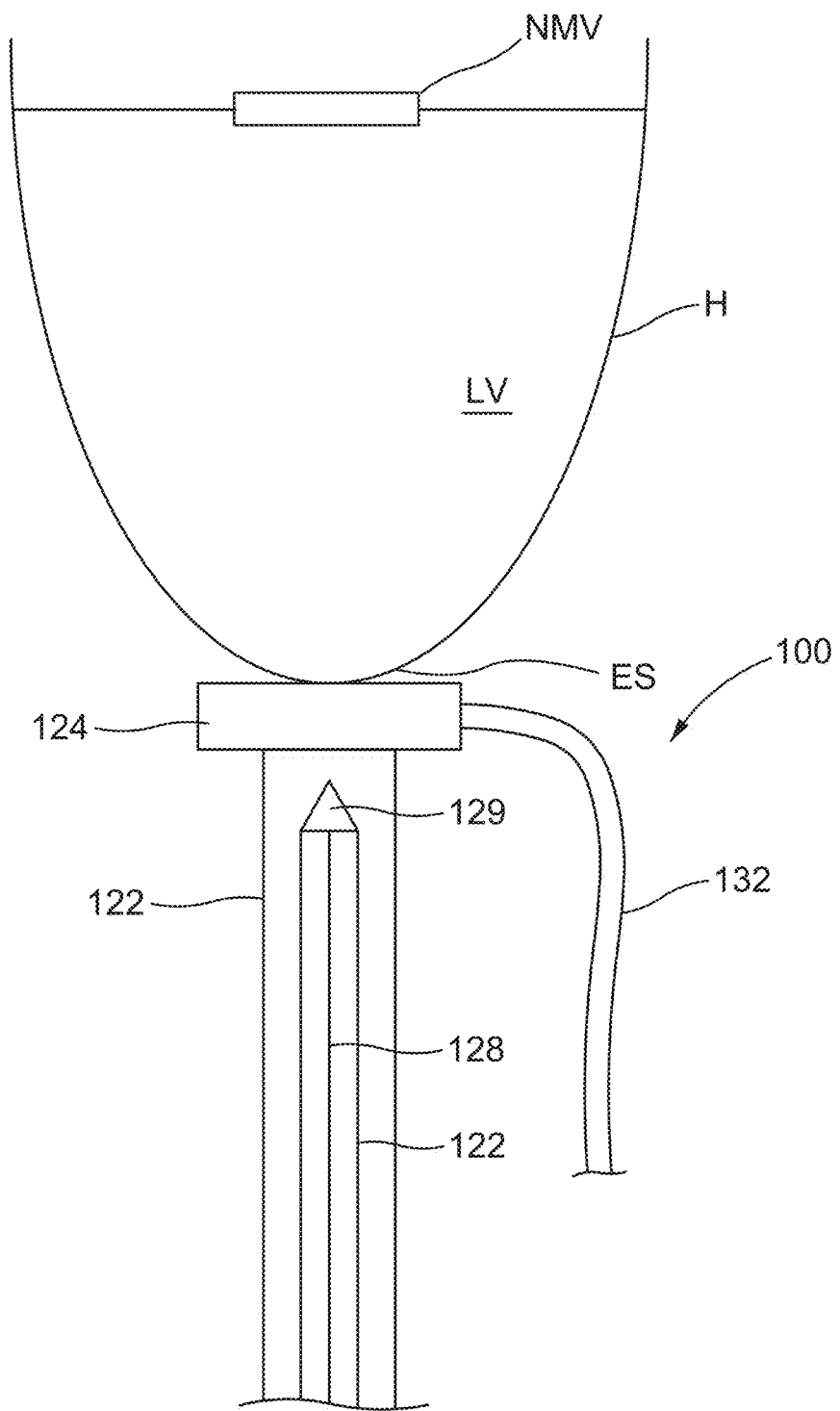
FIG. 2B is a schematic illustration of the alignment device of FIG. 2A shown positioned near an epicardial surface of a heart.

FIG. 2B is a schematic illustration of a portion of the alignment device 100 shown in use to image a heart H. In use, the coupling member 124 is placed near or in contact with the epicardial surface ES of the heart near, for example, the apex of the heart. The imaging element 134 (not shown in FIG. 2B) of the imaging probe 140 can then be used to image the heart to determine an alignment path for a tether attached to the prosthetic valve such that an initial desired location on the apex of the epicardial surface to anchor the tether with an epicardial pad can be determined. For example, images up through the heart can be taken, and the image data can be used to determine an alignment path between the location of the native mitral valve NMV (e.g., a centerline of the mitral valve) and the apex of the heart at the epicardial surface ES. The alignment path can be used to align the tether with the centerline of the native mitral valve and can also be used to guide the needle assembly 120 along the trajectory of the alignment path during a procedure to deploy the prosthetic mitral valve. Using the image data, an optimal or desired location to secure the tether to the epicardial surface can be determined. For example, the optimal location can be substantially perpendicular to the alignment path, which is perpendicular to the C-C plane (described below). Specifically, the imaging probe 140 can produce image data such that the C-C plane and the A-P plane can be identified. For example, alignment device 100 can be placed in a first orientation relative to the heart and first image data can be collected and stored and displayed on the computer device 138. The alignment device 100 can then be rotated, for example, 90 degrees and second image data can be obtained. From this image data, the C-C plane and the A-P plane of the mitral valve and annular region of the heart can be identified. For example, the C-C plane can be identified in the first image data and the A-P plane can be identified in the second image data. For example, the image data can be displayed on a display device of the computer device and a user (e.g., physician) can visually identify the location of the C-C plane/axis and A-P plane/axis. Using the image data produced by the alignment device 100, the user can project an alignment path that is, for example, perpendicular to the C-C plane, and the alignment path can be used to determine the optimal or desired location to secure the tether of a prosthetic mitral valve at the epicardial surface of the heart (e.g., at the apex).

Figure 16:
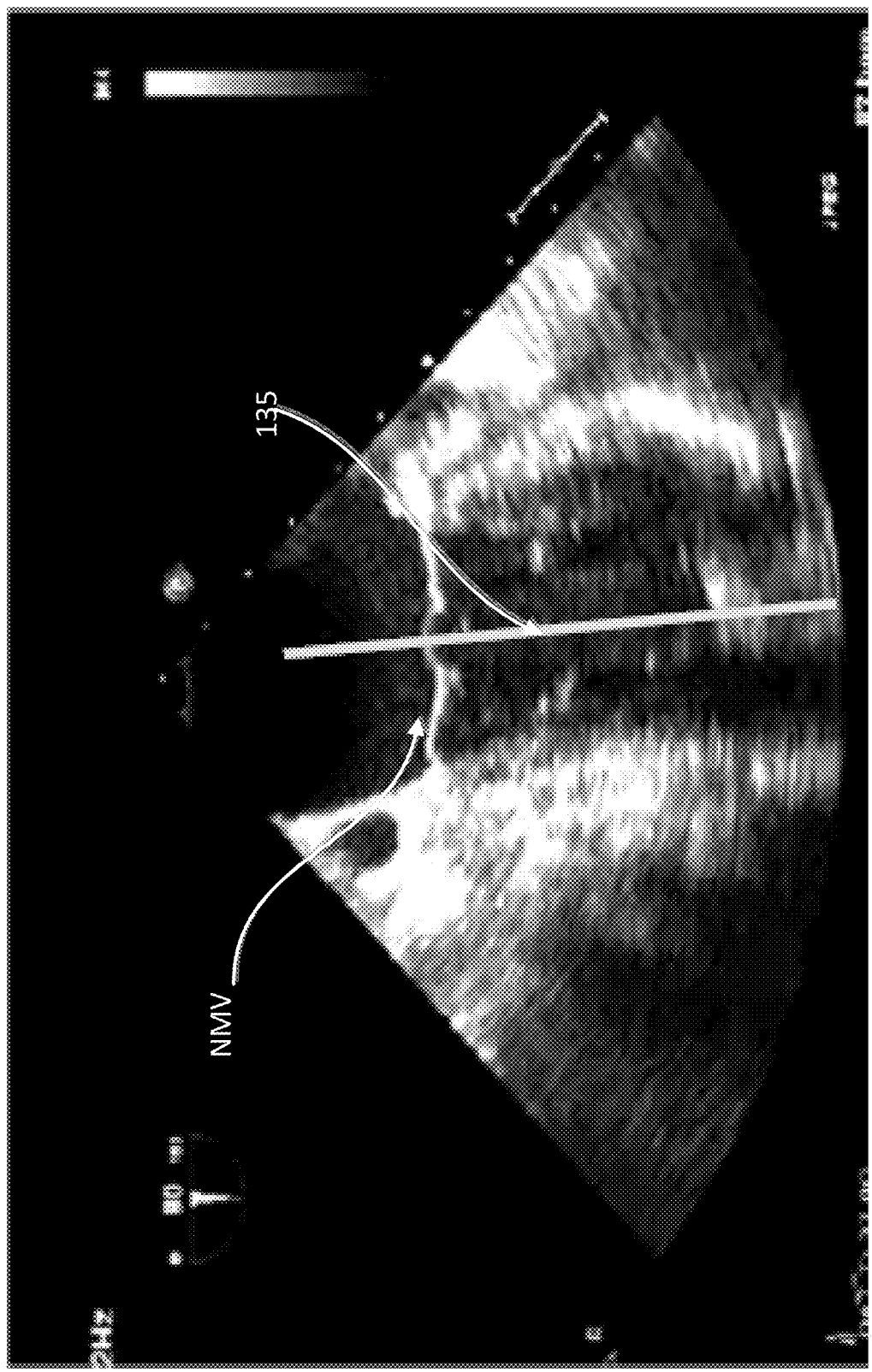
FIGS. 16 and 17 are each a screen shot of an ultrasound image of a heart showing an alignment path projected onto the image.
Figure 17:
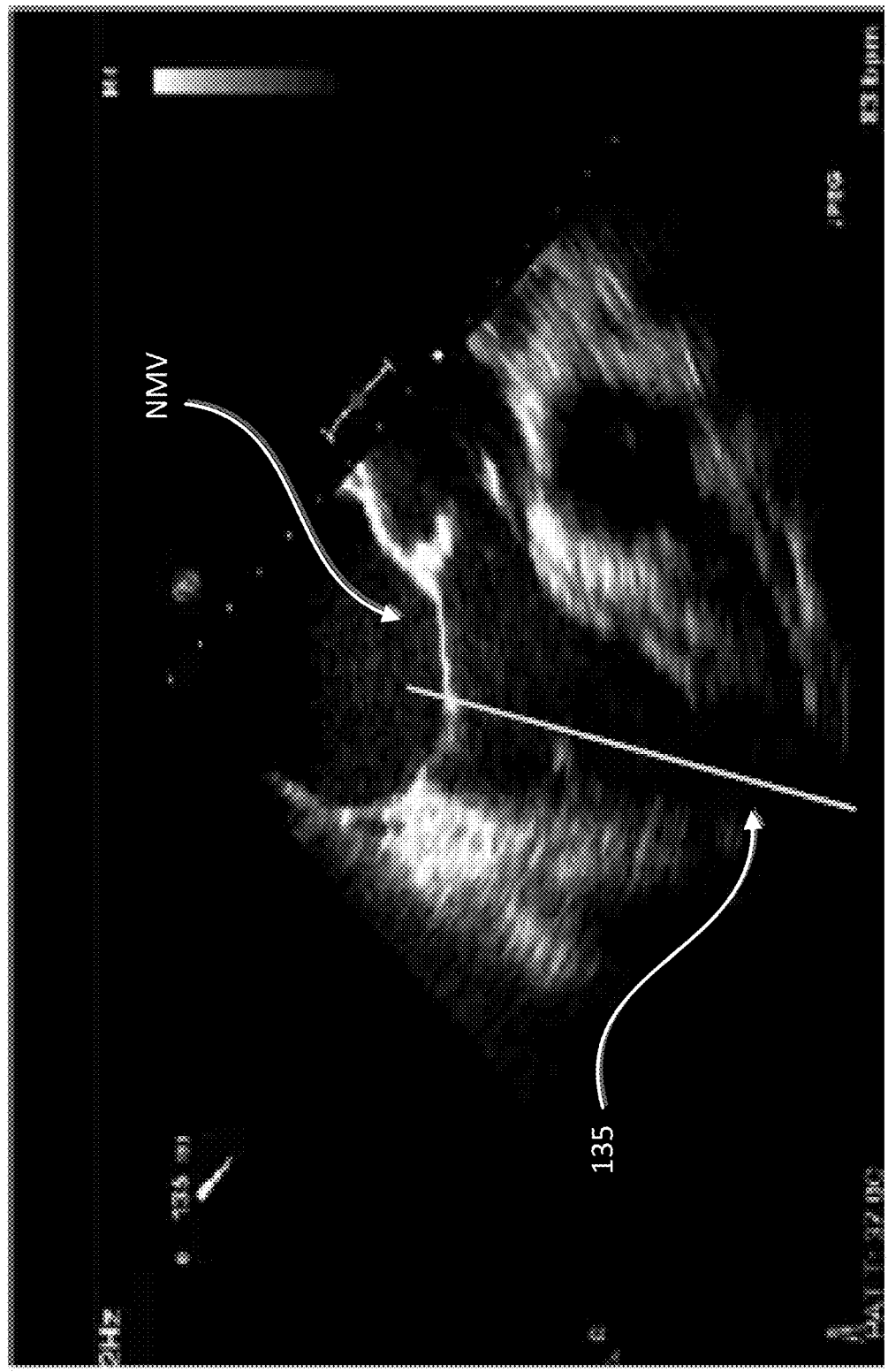

FIGS. 16 and 17 are each an example screenshot of an ultrasound image of the heart that can be produced using the alignment device 100. FIG. 16 is a C-C, mid-esophageal two-chamber view of the heart, produced, for example, with the alignment device positioned at a first orientation relative to the heart. FIG. 17 is an A-P, mid-esophageal long axis view of the heart, produced, for example, with the alignment device 100 positioned at a second orientation relative to the heart 90 degrees from the first orientation. As shown in FIGS. 16 and 17, the C-C plane and the A-P plane can be visually identified and an alignment path 135 can be projected onto the images (e.g., manually by the user) or the user can visually determine an alignment path to use. The alignment path 135 can extend between the C-C plane and the atrioventricular plane of the heart. As shown in FIGS. 16 and 17, the alignment path 135 extends through approximately the center of the native mitral valve NMV. As described above, the alignment path 135 can be used to determine a location to secure a tether of a prosthetic mitral valve to the epicardial surface such that the tether is aligned substantially perpendicular to the C-C plane and the prosthetic mitral valve is perpendicular to the C-C plane.

After the alignment device 100 has been used to obtain the desired image data, and the alignment path (and initial epicardial pad location) and the coordinates for the C-C plane and the A-P plane have been determined, the needle assembly 120 can be moved distally within the outer tube member 122 such that the distal piercing tip 129 of the elongate needle pierces through the epicardial surface at the desired pad location (e.g., determined with the image data described above). The needle assembly 120 can be extended within the left ventricle of the heart along the trajectory of the alignment path. For example, the distal tip 129 of the elongate needle 128 can be disposed distal of the needle tube 126 such that as the needle assembly 120 is moved distally through the outer tube member 122, the distal tip 129 can pierce the epicardial surface and pass through the wall of the heart and within the left ventricle. The elongate needle 128 of the needle assembly 120 can then be removed leaving the needle tube 126 within the heart and extended within the left ventricle. A guidewire (not shown) can then be inserted through the needle tube 126 and positioned within the heart. The needle tube 126 can then be removed from the heart, and the alignment device 100 removed from the patient's body. A prosthetic mitral valve (not shown in FIGS. 2A and 2B) can then be deployed within the atrium using a prosthetic valve delivery device as described in more detail below. The identified C-C plane and A-P plane can then be used to position and align the prosthetic mitral valve and to secure a tether coupled to the prosthetic mitral valve to the epicardial surface using an epicardial pad device.

Figure 3:
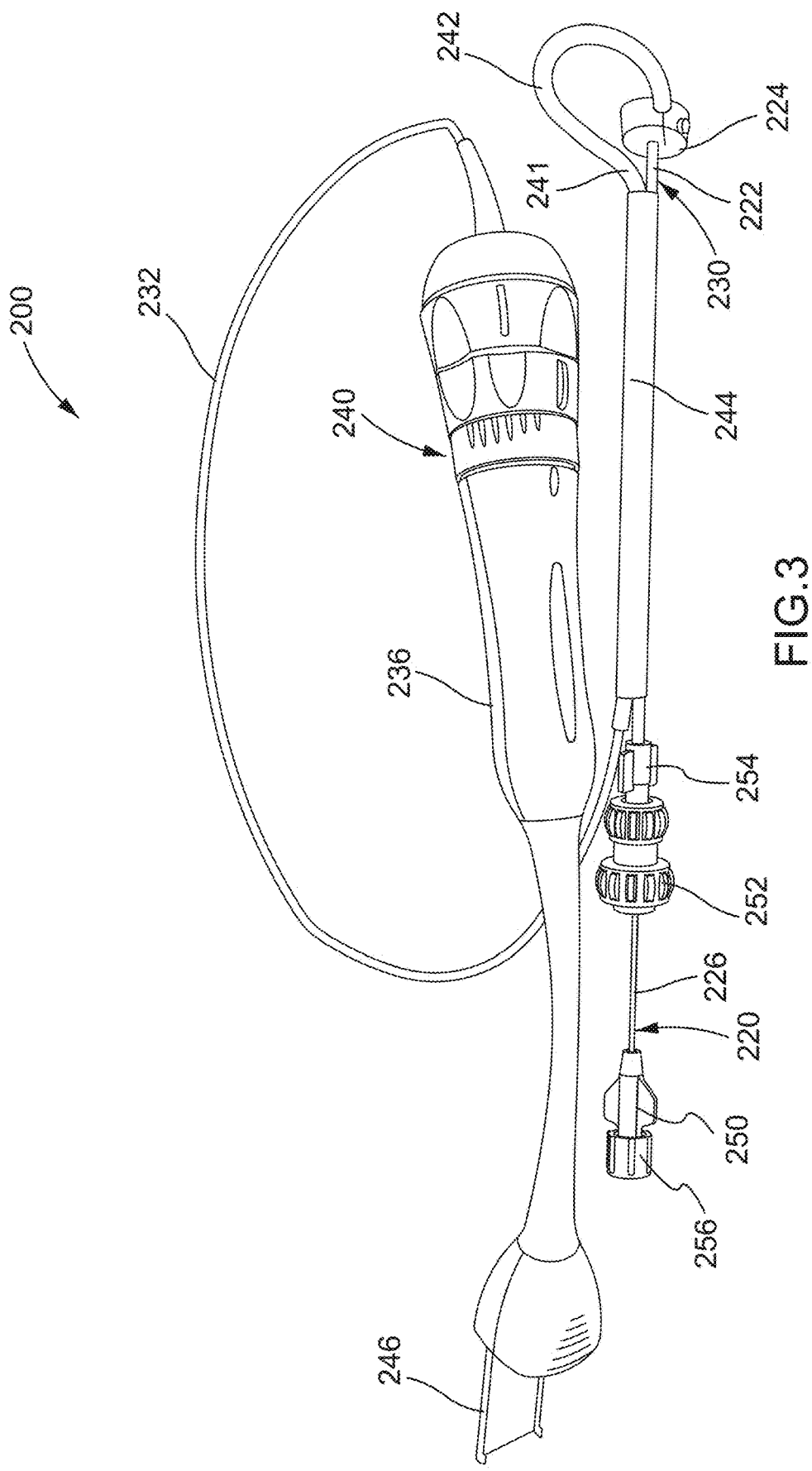
FIG. 3 is a perspective view of an alignment device, according to another embodiment.
Figure 4:
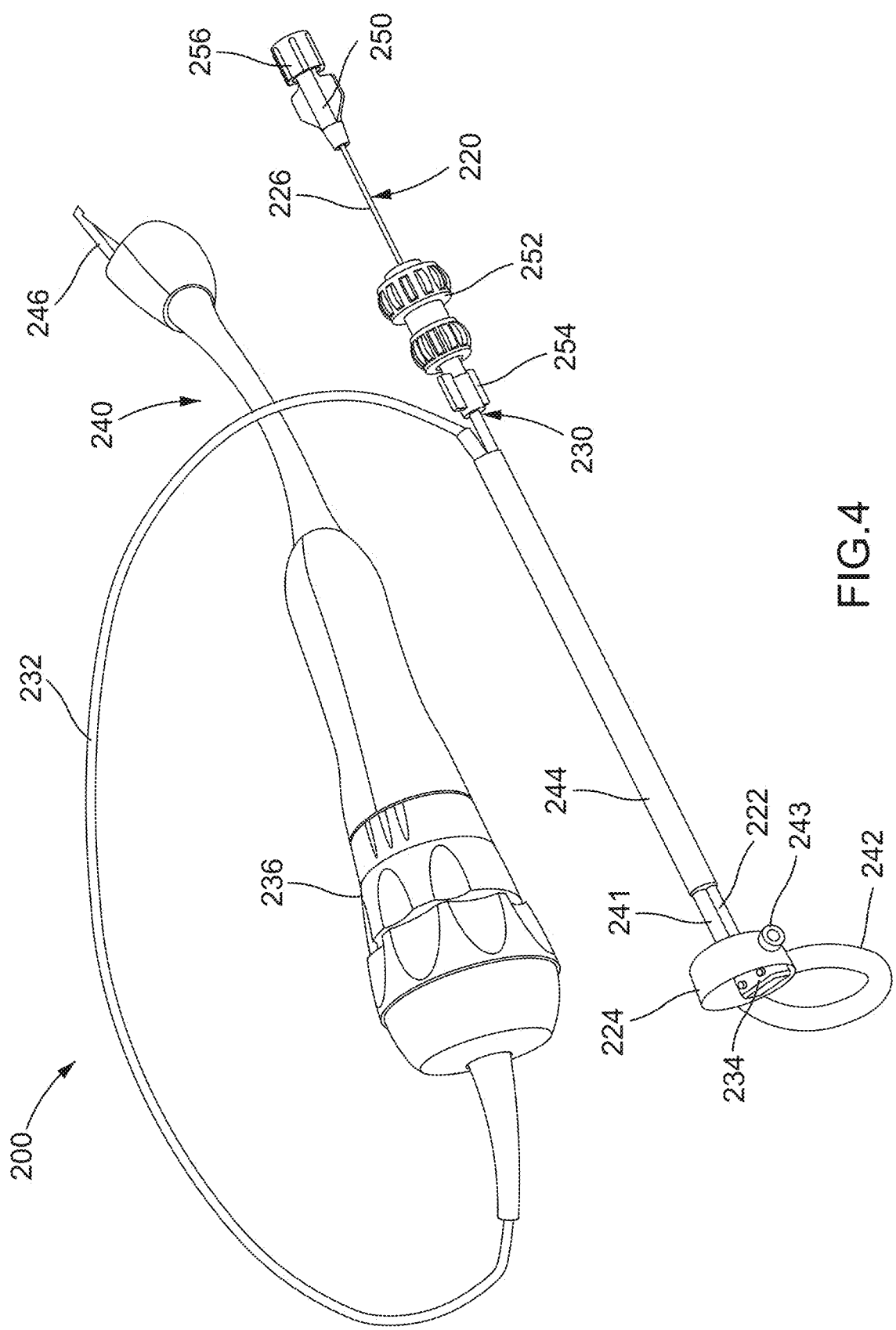
FIG. 4 is another perspective view of the alignment device of FIG. 3.

FIGS. 3 and 4 are each a perspective view of an alignment device 200 according to an embodiment. The alignment device 200 can include the same or similar features and can function the same as or similar to the alignment device 100 and can be used to perform the same or similar procedures as described above for alignment device 100. The alignment device 200 includes a tube assembly 230, a needle assembly 220 and an imaging probe 240. The tube assembly 230 includes an outer tube member 222 and an imaging element coupling member 224 (also referred to herein as "coupling member") coupled to a distal end of the outer tube member 222. The needle assembly 220 is movably received at least partially within a lumen defined by the outer tube member 222 and includes a needle tube 226 and an elongate needle (not shown in FIGS. 3 and 4) that includes a piercing distal tip or stylet (not shown) and an end cap 256 on a proximal end. As shown in FIGS. 3 and 4, the elongate needle and distal tip are retracted within the needle tube 226 and therefore are not visible. The needle assembly 222 includes a needle coupler 250 that can be used to tighten the needle tube 226 to the elongate needle to control or prevent movement of the elongate needle within the needle tube 226 as desired. For example, the needle coupler 250 can have a threaded attachment such that it can be rotated to tighten or loosen the needle tube 226. The needle coupler 250 can be, for example, a luer type connector. A hemostasis valve 252 is coupled to the outer tube member 222 and can be used to prevent bleeding back through the needle system during a procedure. The tube assembly 230 includes a luer connector 254 that is coupled to the outer tube member 222 and is configured to control or prevent movement of the needle assembly 220 within the outer tube member 222 as desired. The imaging element coupling member 224 defines a hole (not shown) through which the elongate needle and distal piecing tip of the needle assembly 222 can pass through and exit the distal end of the alignment device 200.

The imaging probe 240 includes a cable 232 coupled to a handle assembly 236, and an imaging element 234 coupled to a distal end portion of the cable 232. The imaging probe 240 can be the same as or similar to the imaging probe 140 described above. For example, the imaging probe 240 can be a known imaging probe that can be coupled to the tube assembly 230. Similarly, the cable 232, handle assembly 236, and imaging element 234 can each be the same as or similar to, and can provide the same as or similar function as the cable 132, handle assembly 136, and imaging element 134, respectively, described above. In this embodiment, the imaging probe 240 also includes an outer sheath 241 covering a portion of the cable 232 and a distal end portion of the cable 232 forms a targeting loop 242. In use, the targeting loop 242 is configured to contact the epicardial surface of a heart as described in more detail below. The distal end portion of the targeting loop 242 is coupled to the imaging element coupling member 224 and the imaging element 234 (shown in FIG. 4) is coupled to a distal end portion of the targeting loop 242. A screw 243 or other fastener can be used to secure the cable 232 and the imaging element 234 to the imaging element coupling member 224. In this embodiment, a portion of the cable 232 within the outer sheath 241 and a portion of the outer tube member 222 are disposed within a lumen of an outer sleeve component 244.

As with the previous embodiment, the cable 232 electrically and operatively couples the imaging element 234 to control components (not shown) included in the handle 236. As with the previous embodiment, the handle 236 can be operatively coupleable to a computer device (not shown) as described above. For example, the handle 236 includes a connection portion 246 that can be used to electrically couple the imaging probe 240 to a computer device.

As described above for alignment device 100, alignment device 200 can be used during a procedure to deploy a prosthetic heart device, such as, a prosthetic mitral valve. In use, the targeting loop 242 and imaging element coupling member 224 are placed near or in contact with the epicardial surface of the heart. The imaging element 234 of the imaging probe 240 can then be used to image the heart to determine an alignment path for a tether attached to the prosthetic valve such that an initial desired location on the apex of the epicardial surface to anchor the tether with an epicardial pad can be determined as described above for alignment device 100. The imaging probe 240 can also produce image data such that the C-C plane and the A-P plane can be identified as described above.

Also as described above, after the alignment device 200 has been used to obtain the desired image data, and the alignment path (and initial epicardial pad location) and the coordinates for the C-C plane and the A-P plane have been determined, the needle assembly 220 can be moved distally within the outer tube member 222 such that the distal piercing tip of the elongate needle pierces through the epicardial surface at the desired pad location (e.g., determined with the image data described above), and extends to the left ventricle of the heart. For example, the distal tip of the elongate needle can be disposed distal of the needle tube 226 such that as the needle assembly 220 is moved distally through the outer tube member 222, the distal tip can pierce the epicardial surface and pass through the wall of the heart and within the left ventricle. The elongate needle of the needle assembly 220 can then be removed leaving the needle tube 226 within the heart and extended within the left ventricle. A guidewire (not shown) can then be inserted through the needle tube 226 and positioned within the heart. The needle tube 226 can then be removed from the heart, and the alignment device 200 removed from the patient's body. A prosthetic mitral valve can then be deployed within the atrium using a prosthetic valve delivery device as described in more detail below. In some embodiments, a dilator device (not shown) can be used prior to inserting a delivery device to enlarge the opening at the epicardial surface. The identified C-C plane and A-P plane can then be used to position and align the prosthetic mitral valve and to secure a tether coupled to the prosthetic mitral valve to the epicardial surface using an epicardial pad device.

Figure 5B:
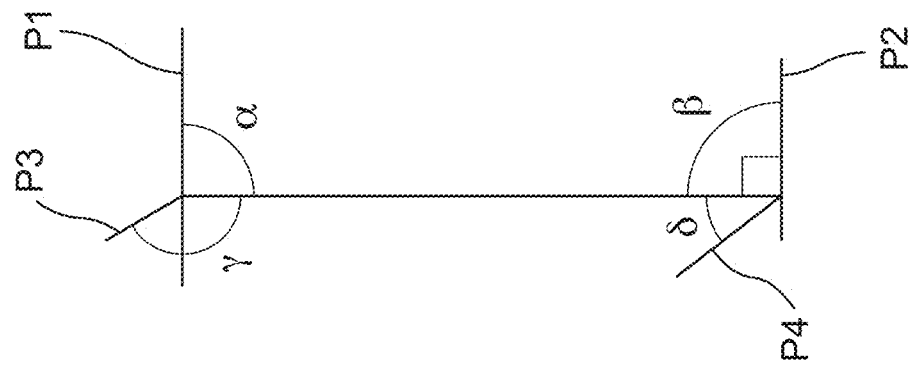
FIG. 5B illustrates the commissural-commissural (C-C) plane and the anterior-posterior (A-P) plane of a mitral valve and annular region of a heart with a tether extending therebetween.
Figure 5A:
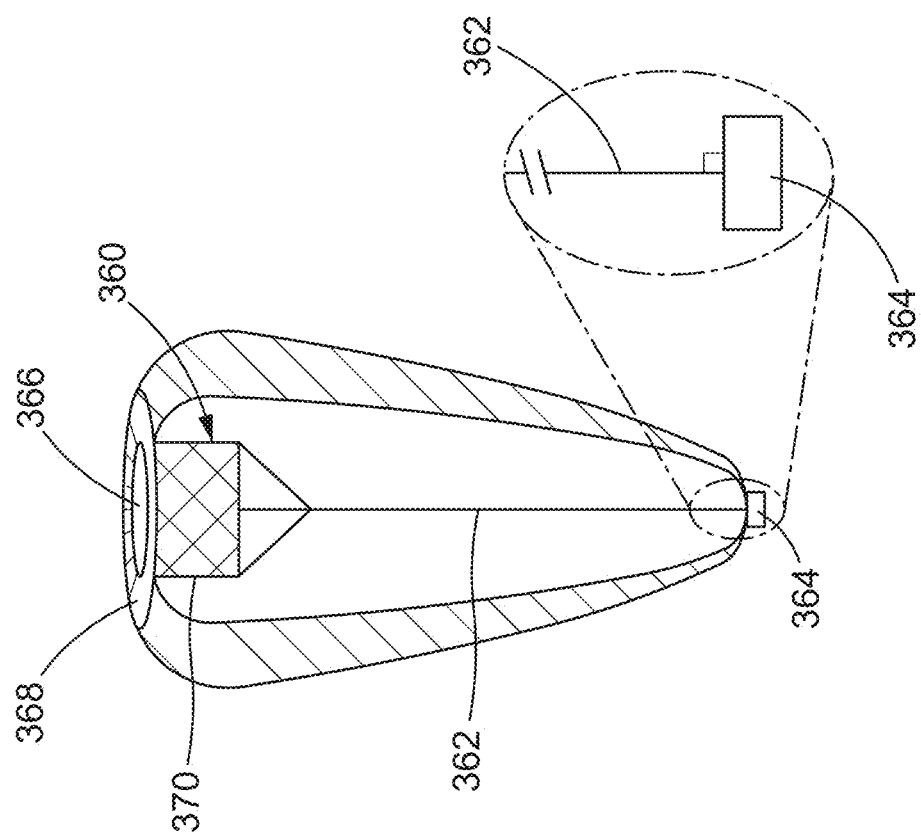
FIG. 5A is a cross-sectional illustration of a portion of a heart with a prosthetic mitral valve deployed into the mitral annulus and having an anchoring tether extending through the ventricle and anchored to the epicardial surface of heart with an epicardial pad device.

FIG. 5A illustrates a prosthetic mitral valve 360 deployed within the mitral annulus in an atrium of a heart and an intraventricular tether 362 (also referred to as "tether") coupled to the prosthetic mitral valve 360 extending through the ventricle exiting an apical aperture and anchored to the epicardial surface with an epicardial pad device 364. In this example, such a prosthetic valve 360 is a compressible self-expanding transcatheter valve and includes a valve lumen 366, a prosthetic valve atrial cuff 368 and a valve body 370. However, it should be understood that the alignment devices described herein can be useful for various other surgical or interventional medical procedures, and particularly for procedures involving the deployment of intracardiac devices. As shown in FIG. 5A, in this example, intraventricular tether 362 is shown as perpendicular to a plane of the epicardial pad device 364 at the point of contact with the epicardial surface, and to the placement of the prosthetic valve.

In procedures involving the deployment of prosthetic mitral valves, having the valve properly seated within the native annulus helps prevent regurgitant leaking. Unlike some known prosthetic valves, a self-expanding prosthetic valve 360 as shown in FIG. 5A does not need to be sewn into place. Historically, in the first generation of artificial valves, such valves were delivered during open heart surgery and the native valve leaflets would be cut away, and a prosthetic valve sewn into place. In such approaches, however, complications can arise from open surgery and sternotomies. Second generation valves were delivered by a cardiac interventionalist, not a surgeon, using a catheter, and required balloon expansion, and were also sewn into place using endoscopic/catheter-based techniques. Third generation valves are characterized by being constructed of self-expanding martensidic/austenitic materials that did not require to be sewn into place. This avoided the problems associated with cardiac remodeling caused by sewing a rigid prosthetic to a dynamic tissue. However, tethering and seating these valves became of utmost importance to avoid leaking during systole.

Proper alignment of prosthetic valves in the C-C commissural plane/axis and the A-P anterior-posterior plane/axis can reduce and/or avoid perivalvular leakage around such prosthetic valves. However, the mitral valve is known to have a highly complex three-dimensional shape, namely a hyperbolic paraboloid, or more commonly, the shape of a well-known stackable potato chip. Another problem concerns LVOT obstruction. Prosthetic valves that apply significant lateral pressure against the anterior portion of the annulus can cause obstruction of the aortic flow exiting the left ventricle because the mitral annulus and the aorta share a common wall at the anterior segment of the mitral valve. The consequence of this is that sealing against perivalvular leaking while avoiding LVOT can be a challenge. Thus, fourth generation devices have implemented an asymmetric design to accommodate the seating of the prosthetic valve into the native annulus, while at the same time eliminating the lateral annular pressure that causes LVOT obstruction. But this raises another issue, namely, that the prosthetic valve, now asymmetric, must be deployed so that the axis of the valve features is in alignment with the axis of the mitral annulus.

Referring now to FIG. 5B, which is a schematic illustration showing the commissural-commissural (C-C) plane/axis, labeled P1, the apical lateral plane/axis, labeled P2, the anterior-posterior plane/axis, labeled P3, and the apical longitudinal plane/axis, labeled P4. As shown, in this example, the plane/axis P1 is substantially parallel to the plane/axis P2 such that tether 362 intersects both the plane/axis P1 and the plane/axis P2 at substantially 90 degree angles. The plane/axis P3 is also shown to be substantially parallel to the plane/axis P4. The angles alpha $\alpha$ (between tether 362 and plane/axis P1), beta $\beta$ (between tether 362 and P2), gamma $\gamma$ (between tether 362 and P3), and delta $\delta$ (between tether 362 and P4), can vary, for example, according to ranges of 85 to 95 degrees, 80 to 100 degrees, and 75 to 105 degrees. The angle relationship between the planes/axis P1 and the plane/axis P2, and the angle relationship between the plane/axis P3 and the plane/axis P4 can also vary accordingly from being parallel as shown, depending on the particular anatomy encountered with a given patient.

Figure 6A:
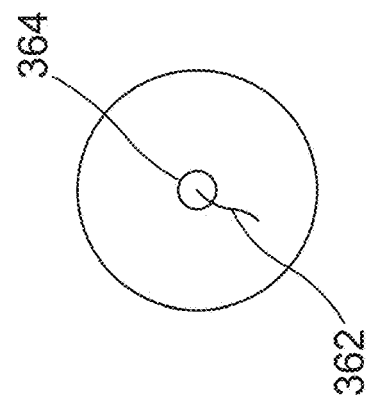
FIGS. 6A-6D are schematic illustrations showing various views of the prosthetic mitral valve and tether of FIG. 5A deployed within a heart.
Figure 6B:
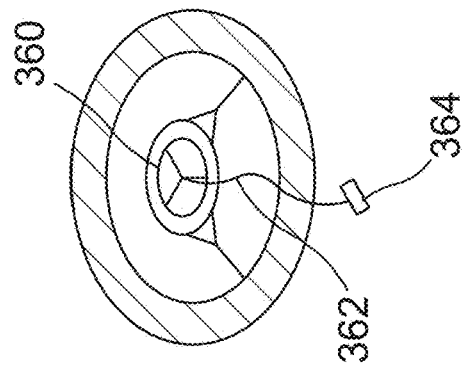
Figure 6C:
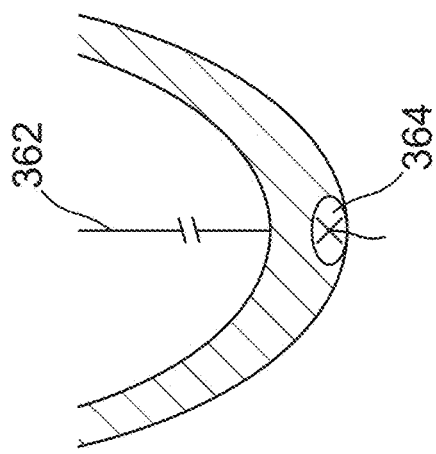
Figure 6D:
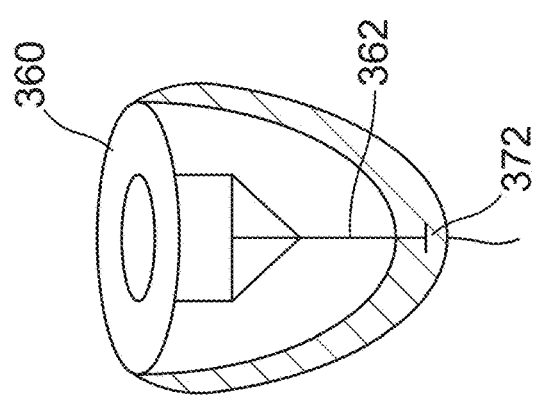

FIGS. 6A-6D illustrate a series of schematic sectional views showing the prosthetic valve and tether deployed within the heart. FIG. 6A shows a prosthetic mitral valve 360 deployed within the mitral annulus in the atrium of the heart and the intraventricular tether 362 extending through the floor/apex 372 of the ventricle. FIG. 6B shows an epicardial view showing the epicardial pad 364 affixed to the apical surface of the heart, and the tether 362 coupled to the pad 364 through the ventricle. FIG. 6C shows a view of the left ventricle showing the bottom of the prosthetic valve body 370 that is deployed in the native annulus, and the tether 362 extending intraventricularly away from valve 360 towards the apex 372 and pad 364. FIG. 6D is an apical view of the heart showing the epicardial pad 364 affixed to the epicardial surface with the tether 362 tied off and trimmed.

Figure 7:
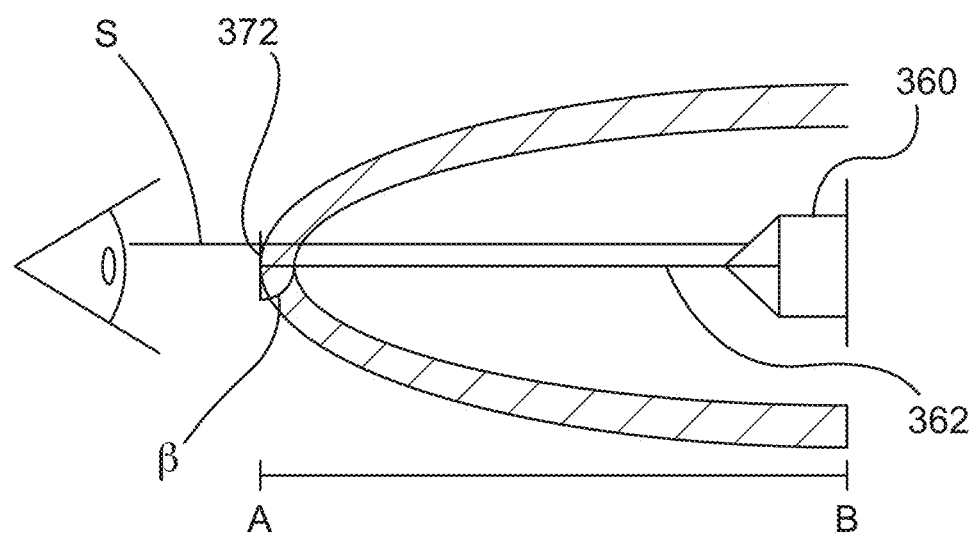
FIG. 7 is a schematic illustration showing a line of sight between the commissural-commissural (C-C) plane and the anterior-posterior (A-P) plane of the mitral valve and tether of FIGS. 6A-6D deployed within the heart.
Figure 8:
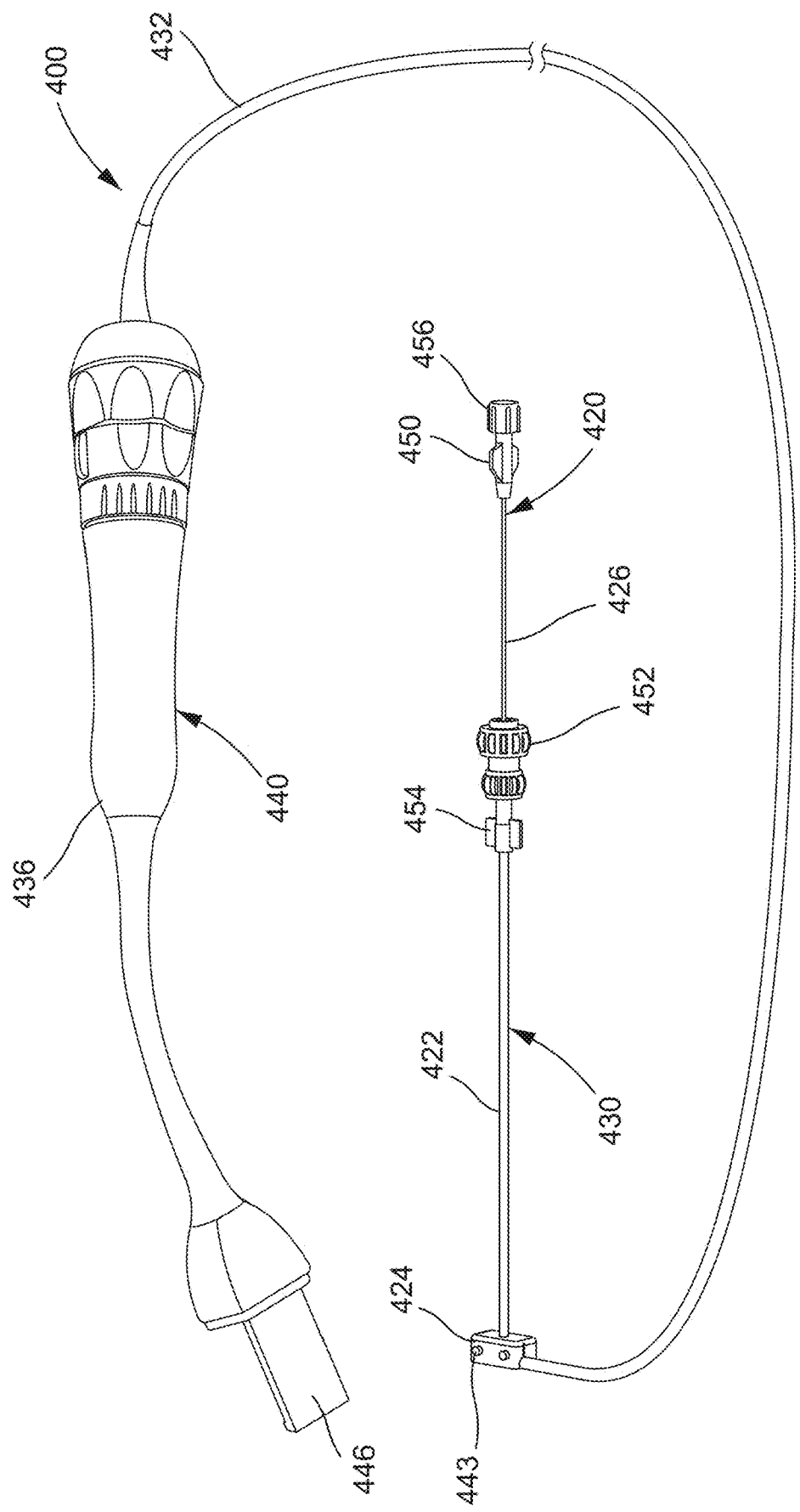
FIG. 8 is a plan view of an alignment device, according to another embodiment.
Figure 9:
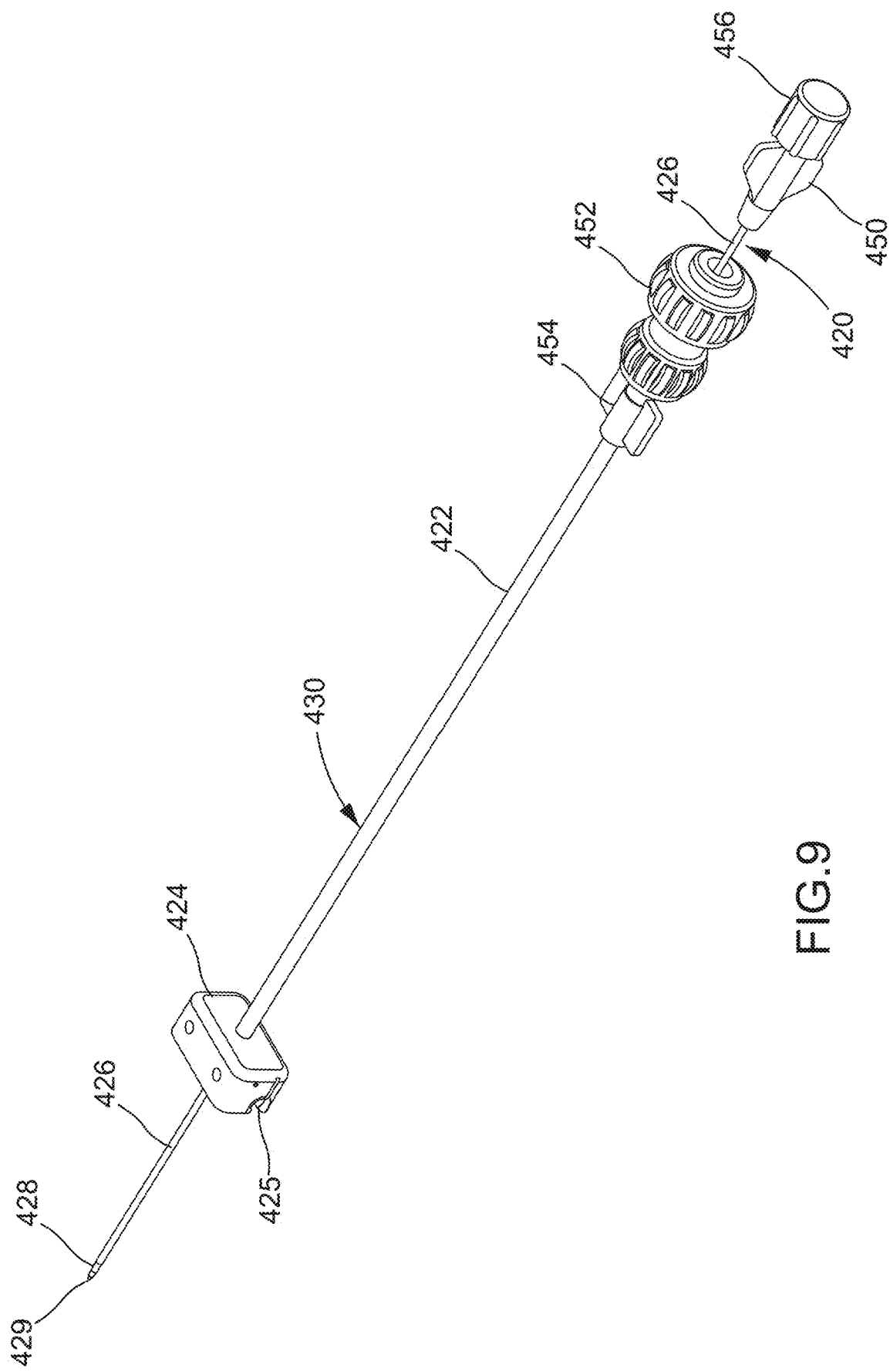
FIG. 9 is a perspective view of a portion of the alignment device of FIG. 8.
Figure 10:
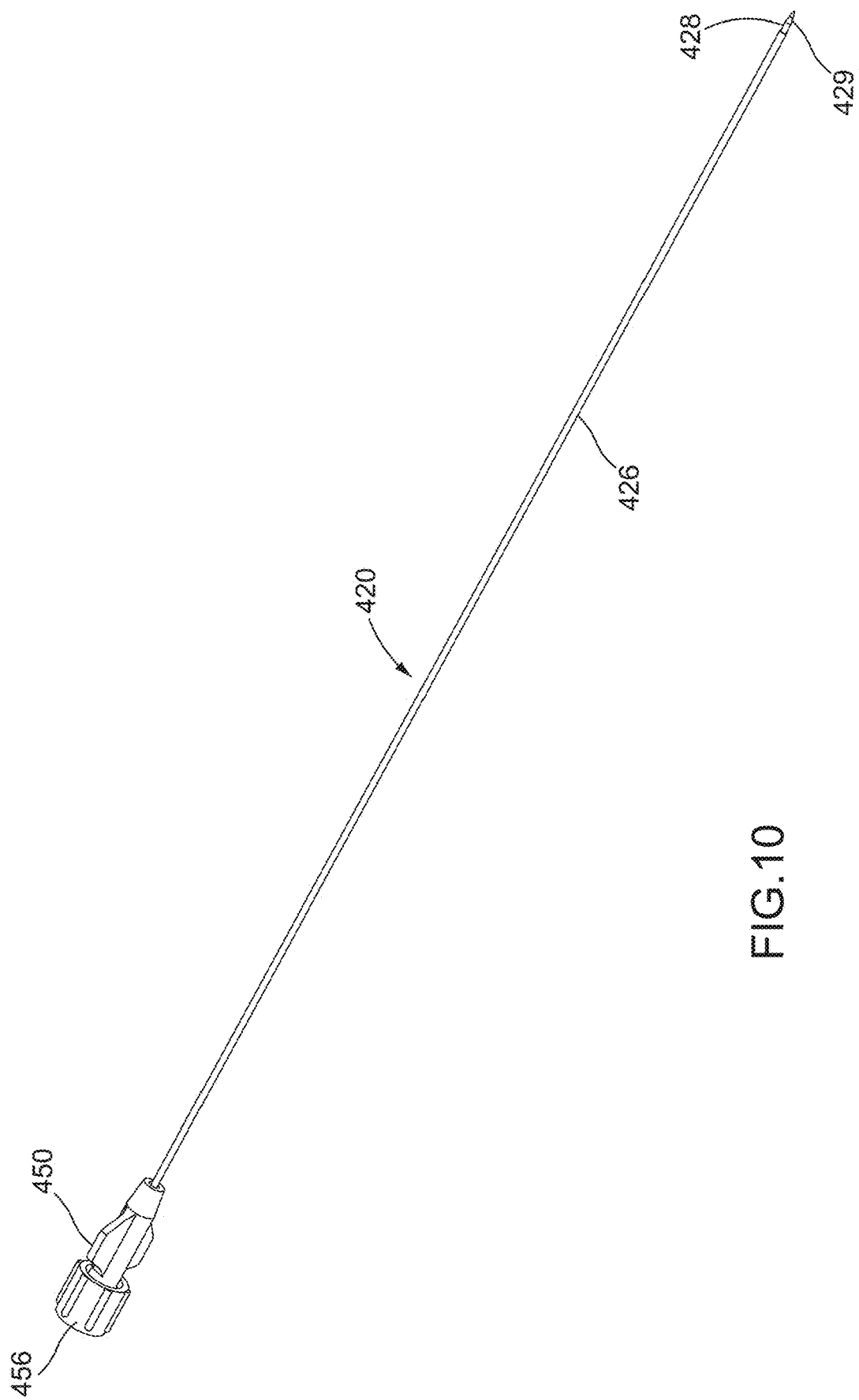
FIG. 10 is a perspective view of a needle assembly of the alignment device of FIG. 8.
Figure 11:
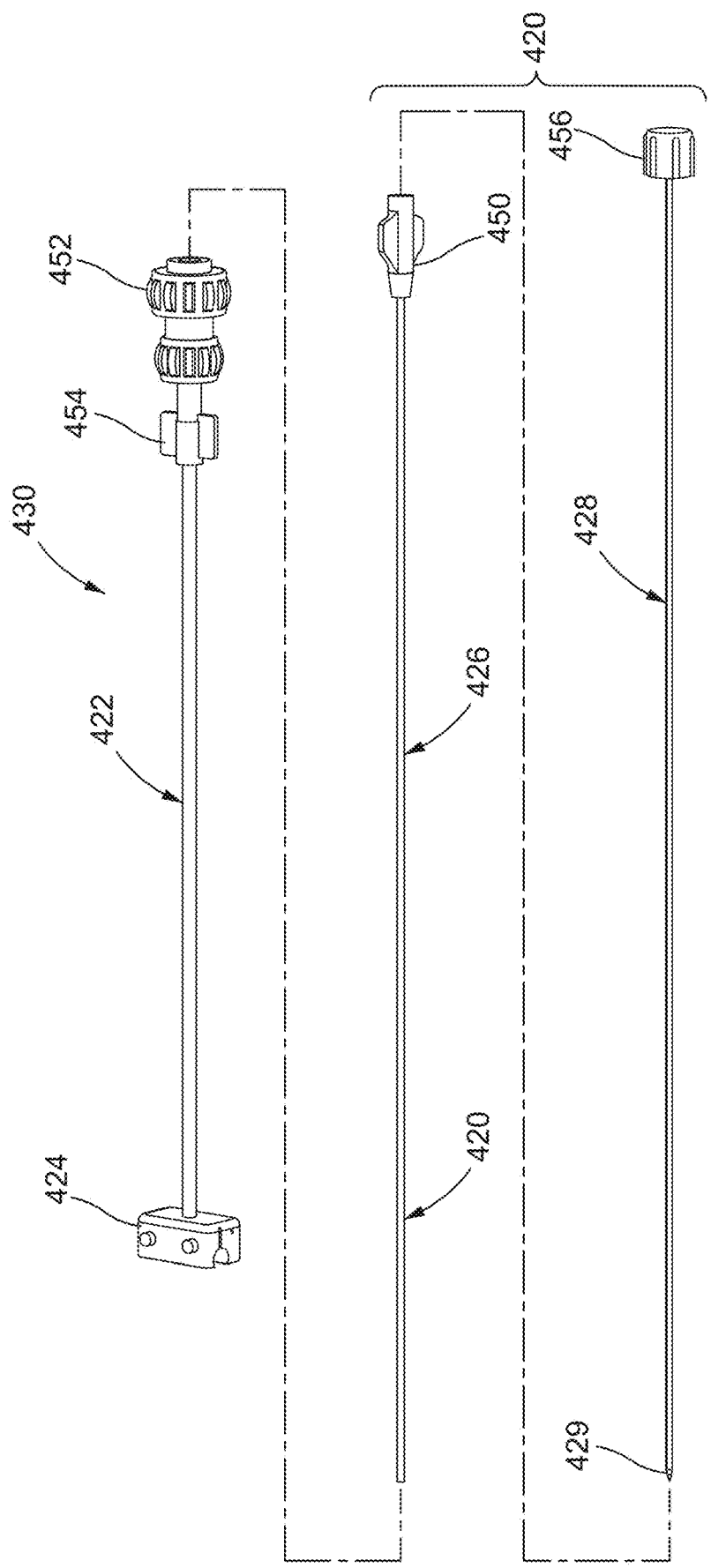
FIG. 11 is a side view of the needle assembly disassembled and the tube assembly of the alignment device of FIG. 8.
Figure 12:
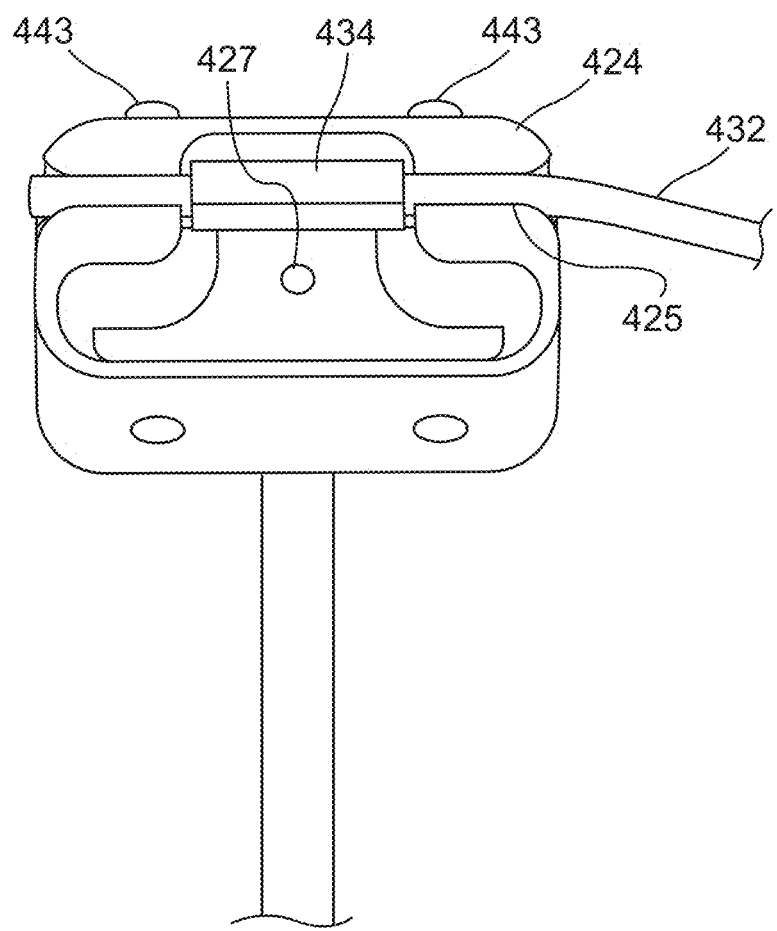
FIG. 12 is an enlarged perspective view of a portion of the alignment device of FIG. 8 showing the cable and imaging element coupled to the imaging element mounting member.

FIG. 7 is a cross-sectional side view illustration of the intended final alignment of the deployed valve 360. FIG. 7 shows the ventricular wall in cross-section with a sight-line S with point A-to-point B extending from the ventricular apex 372 along tether 362 towards the atrium and commissural plane/axis P1. The angle, beta $\beta$, near the apex 372 is shown as one of the useable angles for maximizing the anti-leaking property of the properly deployed valve 360. Another benefit, aside from preventing leakage, is reducing or preventing tissue damage at the apex 372.

FIGS. 8-12 illustrate an alignment device according to another embodiment. An alignment device 400 can include some or all of the same or similar features, and can function the same as or similar to, the alignment devices 100, 200 or 300 described above, and can be used to perform the same or similar procedures. The alignment device 400 includes a tube assembly 430, a needle assembly 420 and an imaging probe 440. The tube assembly 430 includes an outer tube member 422 and an imaging element coupling member 424 coupled to a distal end of the outer tube member 422. The needle assembly 420 is movably received at least partially within a lumen defined by the outer tube member 422 and includes a needle tube 426 and an elongate needle 428 (see FIG. 11) that includes a piercing distal tip or stylet 429 and an end cap 456 on a proximal end. The needle assembly 422 also includes a needle coupler 450 that can be used to tighten the needle tube 426 to the elongate needle 428 to control or prevent movement of the elongate needle 428 within the needle tube 426 as desired. For example, the needle coupler 450 can have a threaded attachment such that it can be rotated to tighten or loosen the needle tube 426. The needle coupler 450 can be, for example, a luer type connector. A hemostasis valve 452 is coupled to the outer tube member 422 and can be used to prevent bleeding back through the alignment device 400 during a procedure. The tube assembly 430 includes a luer connector 454 that is coupled to the outer tube member 422 and is configured to control or prevent movement of the needle assembly 420 within the outer tube member 422 as desired. The imaging element coupling member 424 defines a hole 427 (see, e.g., FIG. 12) through which the elongate needle 428 and distal piecing tip 429 of the needle assembly 422 can pass and exit the distal end of the alignment device 400.

The imaging probe 430 includes a cable 432 coupled to a handle assembly 436, and an imaging element 434 (e.g., one or more transducers) coupled to a distal end portion of the cable 432. The imaging probe 440 can be the same as or similar to the imaging probes 140 and 240 described above. For example, the imaging probe 440 can be a known imaging probe that can be coupled to the tube assembly 430. Similarly, the cable 432, handle assembly 436, and imaging element 434 can each be the same as or similar to, and can provide the same as or similar function as the cable 132, handle assembly 136 and imaging element 134, respectively, described above for previous embodiments. The distal end portion of the cable 432 with the imaging element 434 is coupled to the imaging element coupling member 424 as shown, for example, in FIG. 12. For example, the distal end portion of the cable 432 can be received within a groove 425 defined by the imaging element coupling member 424. A pair of screws 443 or other fasteners can be used to secure the cable 432 and imaging element 434 to the imaging element coupling member 424.

As with the previous embodiments, the cable 432 electrically and operatively couples the imaging element 434 (transducer(s)) to control components (not shown) included in the handle 436. Also as with the previous embodiments, the handle 436 can be operatively coupleable to a computer device (not shown) as described above. For example, the handle 436 includes a connection portion 446 that can be used to electrically couple the imaging probe 440 to a computer device.

As described above for alignment devices 100 and 200, alignment device 400 can be used during a procedure to deploy a prosthetic heart device, such as, a prosthetic mitral valve. In use, the imaging element coupling member 424 is placed near or in contact with the epicardial surface of the heart. The imaging element 434 of the imaging probe 440 can then be used to image the heart such that the image data collected can be used to determine an initial desired location to secure a tether attached to the prosthetic mitral valve at the epicardial surface with an epicardial pad, and the C-C plane/axis and the A-P plane/axis can be identified. For example, the image data can be displayed on a display device of the computer device and the C-C plane and A-P plane can be viewed by a user. After the alignment device 400 has been used to obtain the desired image data, and the location for the epicardial pad and the coordinates for the C-C plane and the A-P plane have been determined, the needle assembly 420 can be moved distally within the outer tube member 422 such that the distal piercing tip of the elongate needle pierces through the epicardial surface and extends within the left ventricle of the heart. For example, the distal tip of the elongate needle can be disposed distal of the needle tube 426 such that as the needle assembly 420 is moved distally through the outer tube member 422, the distal tip can pierce the epicardial surface and pass through the wall of the heart. The elongate needle can then be removed leaving the needle tube 426 within the heart and extended within the left ventricle to the native mitral valve. A guidewire (not shown) can then be inserted through the needle tube 426 and positioned within the heart. The guidewire can be advanced through the atrium and anchored to a suitable location within the heart, such as, for example, to the pulmonary vessel area. A balloon can be used in conjunction with the guidewire to avoid having the guidewire interfere with the chordae tendineae, which are found in the ventricle below the mitral valve. The needle tube 426 can then be removed from the heart, and the alignment device 400 removed from the patient's body. A prosthetic mitral valve can then be deployed within the atrium using a prosthetic valve delivery device as described in more detail below. The identified C-C plane and A-P plane can then be used to position and align the prosthetic mitral valve and to secure a tether coupled to the prosthetic mitral valve to the epicardial surface using an epicardial pad device.

Figure 13:
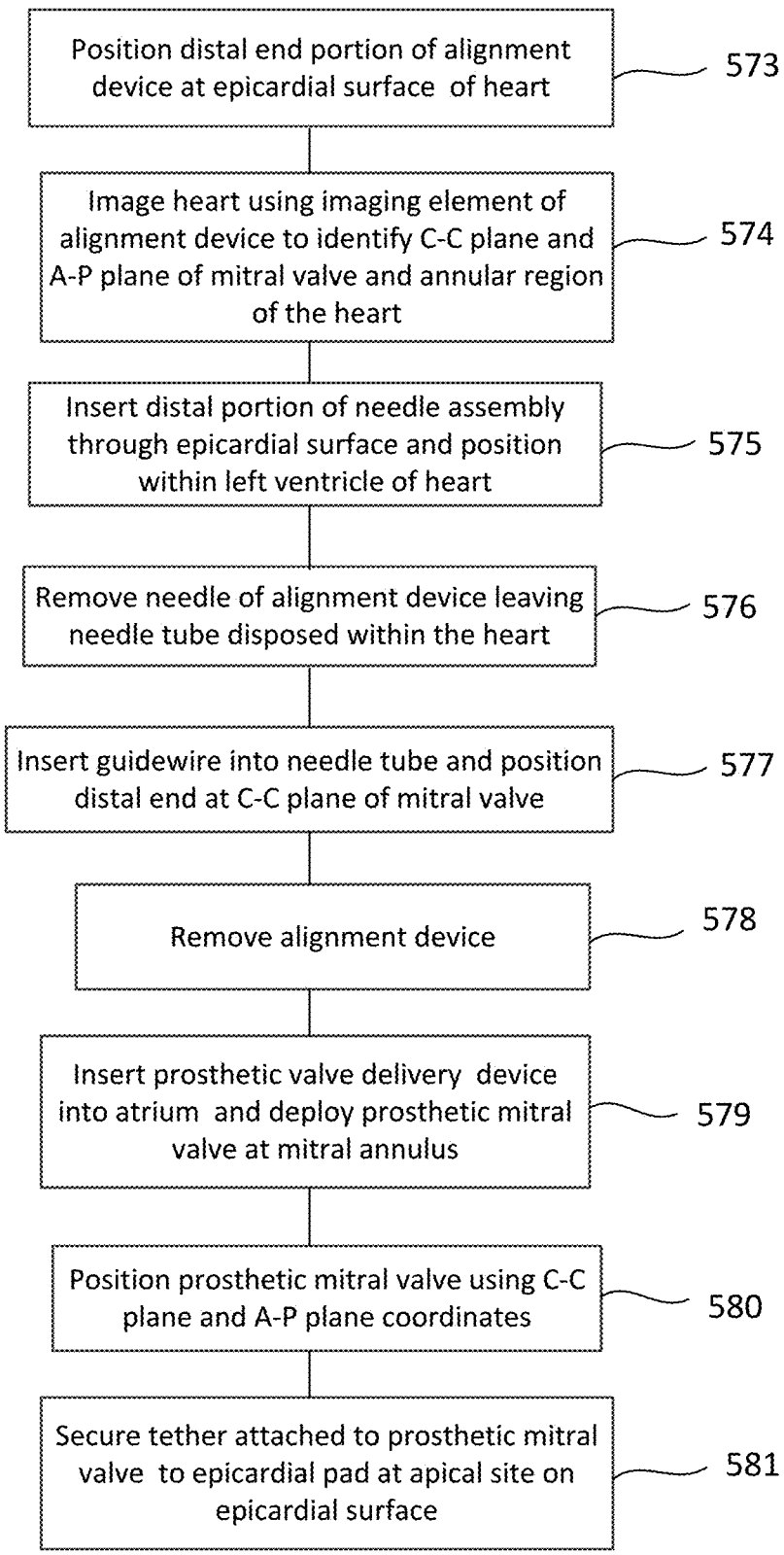
FIG. 13 is a flowchart illustrating a method of deploying and aligning a prosthetic mitral valve, according to an embodiment.

FIG. 13 is a flowchart illustrating a method of deploying and aligning a prosthetic valve within a heart using an alignment device as described herein. At 573, a distal end portion of an alignment device as described herein is positioned near or in contact with an epicardial surface of a heart. At 574, the heart is imaged using an imaging element of the alignment device to identify the C-C plane and A-P plane of the mitral valve and annular region of the heart. At 575, a needle assembly of the alignment device is inserted through the epicardial surface and extended within the left ventricle. At 576, an elongate needle of the alignment device is removed leaving a needle tube disposed within the heart. At 577, a guidewire is inserted into the needle tube and a distal end is positioned or anchored to tissue at or near the C-C plane of the native mitral valve. For example, the guidewire can be anchored to, for example, the pulmonary vessel area. At 578, with the guidewire in position in the heart, the alignment device can be removed. At 579, a prosthetic valve delivery device is inserted over the guidewire and into the atrium of the heart to deploy a prosthetic mitral valve at the mitral annulus. At 580, the prosthetic mitral valve is positioned using the C-C plane and A-P plane coordinates determined by the imaging data produced by the alignment device. At 581, a tether attached to the prosthetic mitral valve is secured at an apical site on the epicardial surface with an epicardial pad.

Figure 14:
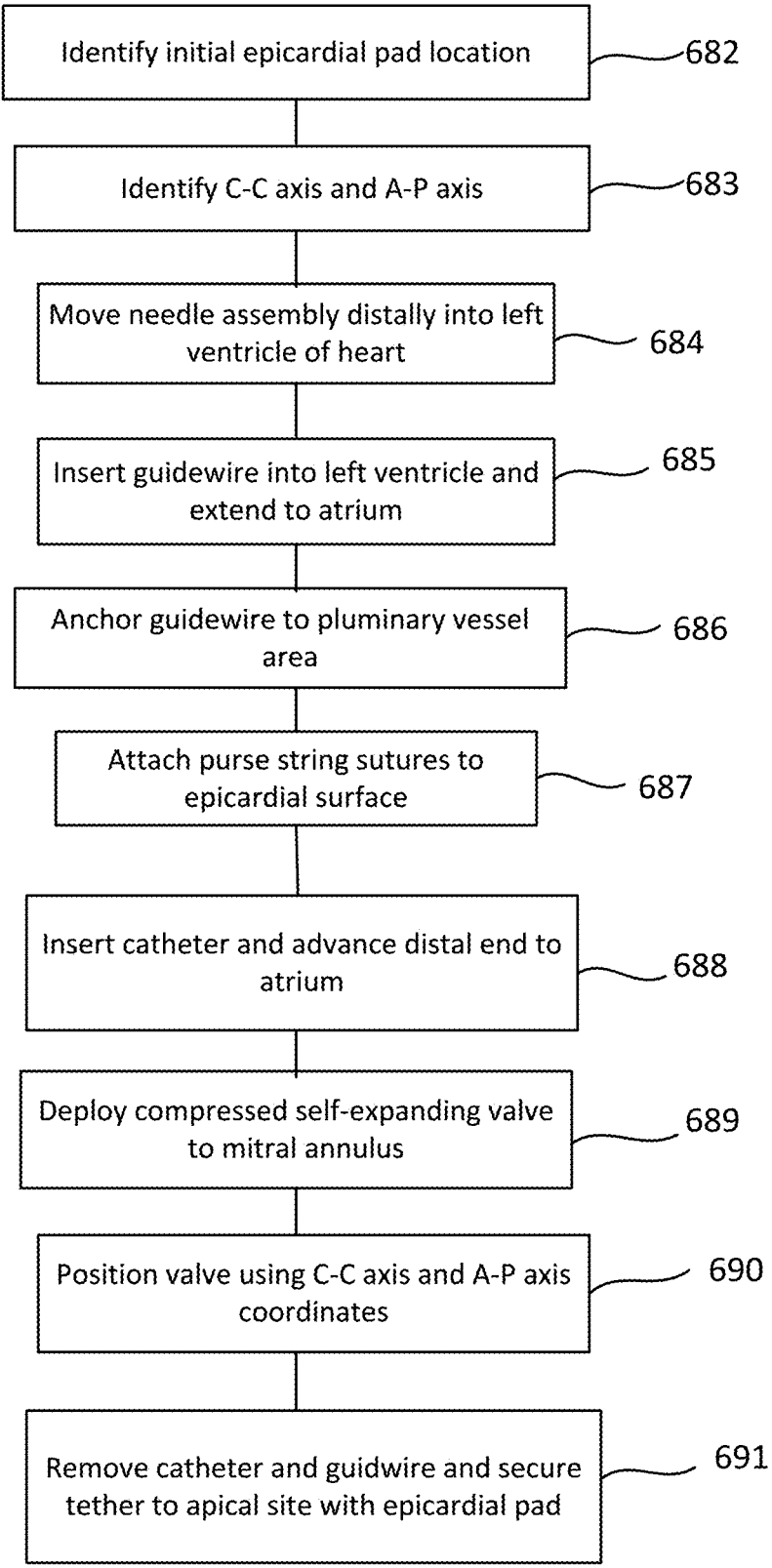
FIG. 14 is a flowchart illustrating another method of deploying and aligning a prosthetic mitral valve, according to an embodiment.
Figure 15:
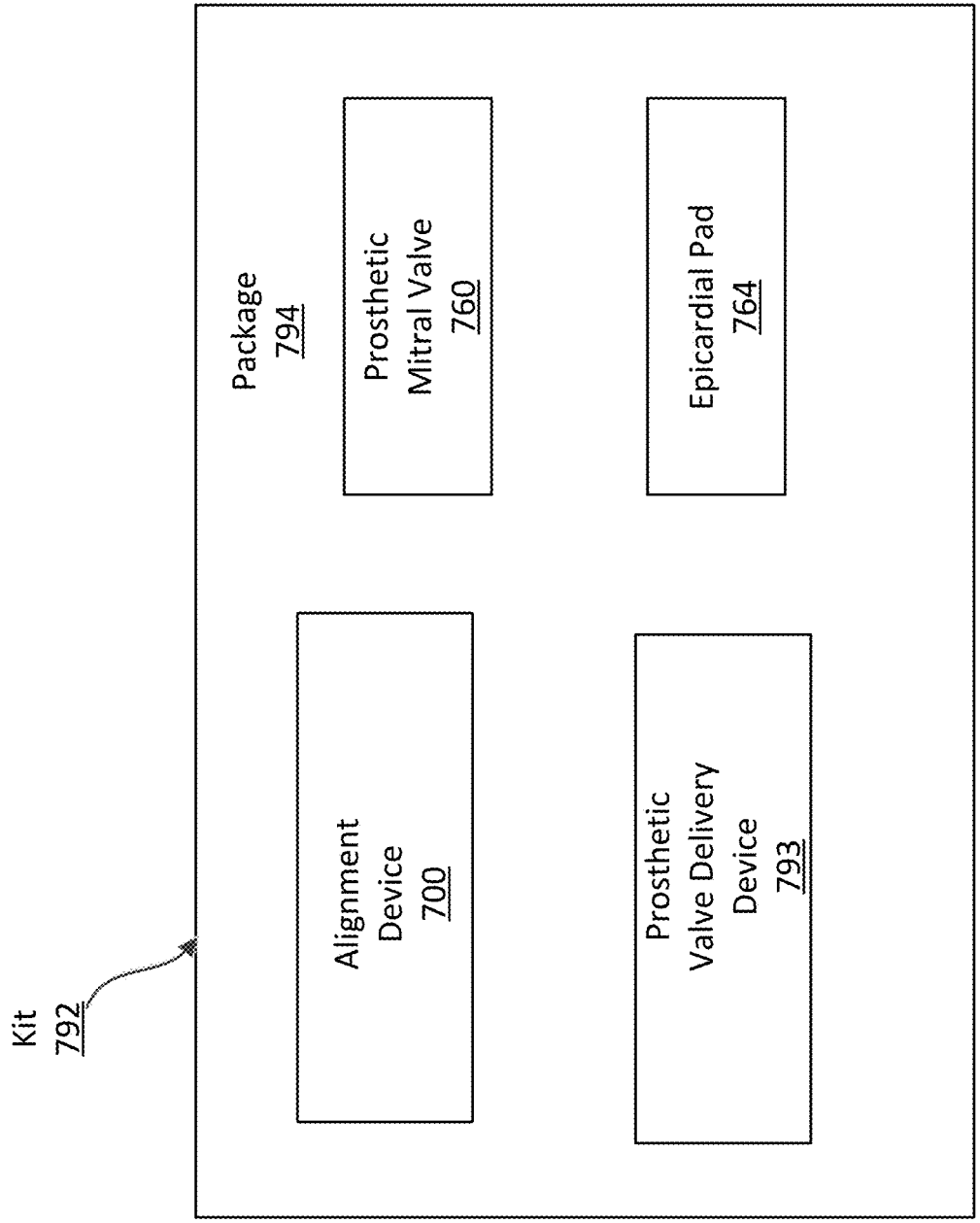
FIG. 15 is a schematic illustration of a mitral valve deployment and alignment kit, according to an embodiment.

FIG. 14 is a flowchart illustrating another method of deploying a prosthetic valve using an alignment device as described herein in conjunction with a prosthetic valve delivery device. At 682, the initial epicardial pad location is identified using an alignment device as described herein. At 683, the commissural-commissural (C-C) axis and anterior-posterior (A-P) axis of the mitral valve and annular region are identified. At 684, the proper axis of insertion is identified and the needle assembly is moved distally through the tube assembly (e.g., 130, 230, 430) and through the apical ventricular wall. At 685, the elongate needle of the needle assembly is removed, leaving the needle tube in position within the heart, and a guidewire is inserted through the needle tube and into the ventricle, and extended to the atrium. A balloon can optionally be used to avoid having the guidewire interfere with the chordae tendinae, which are found in the ventricle below the mitral valve. At 686, the guidewire is extended up through the atrium and anchored to a suitable location such as the pulmonary vessel area, and the balloon is removed. A dilator can be inserted onto the wire and into the ventricle. At 687, purse string sutures can be attached to the identified apical access site on the epicardial surface. At 688, a catheter (e.g., valve delivery device) is inserted into the atrium. The catheter is loaded with a prosthetic valve, such as a self-expanding tethered cuffed valve described herein. At 689, the compressed (compressed within the catheter or delivery capsule) self-expanding asymmetric transcatheter valve is deployed into the mitral annulus. At 690, an echoradiography or other suitable imaging technique can be used to position the asymmetric valve using the C-C and A-P axis coordinates, which can ensure that the flat(ter) portion of the valve cuff is oriented towards the A2 leaflet and any anti-leakage cuff features are placed within the commissures. At 691, the deployment device catheter and the guidewire can be removed. The tether that is attached to the prosthetic valve can provide a longitudinal sealing force towards the apex, and the tether can be secured to an epicardial pad device at the apical site. In some embodiments, a vacuum low pressure may be applied to provide a temporary positioning seal to affix the probe against the epicardial surface and maintain a correct location once the correct epicardial location is identified under radiography FIG. 15 is a schematic illustration of a kit according to an embodiment. In some embodiments, a surgical kit 792 can include an alignment device 700 which can be, for example, an alignment device as described herein (e.g., alignment device 100, 200, 400) and a transcatheter prosthetic valve delivery device 793 both disposed within a sterile package 794. In some embodiments, the kit 792 can further include a transcatheter valve 760 (e.g., a prosthetic mitral valve) and/or an epicardial pad 764 that can be used to secure the transcatheter valve 760 in position within the heart. The kit 792 can also include other optional components such as, for example, a guidewire and/or a dilator device (each not shown in FIG. 15).

An epicardial pad device (also referred to as "pad" or "pad device") as described herein may be a common pledget or similar device, or can be a device having multiple subcomponents. In one embodiment, the epicardial pad device may include a flexible pad for contact with the epicardial surface, a sleeve gasket, and a rigid suturing disk as described, for example, in PCT application '049218 incorporated by reference above. Such a flexible pad is intended for contacting the epicardial surface and may be constructed of any suitable biocompatible surgical material. The pad functions to assist sealing of the surgical puncture. In some embodiments, the pad device can be made at least in part of a double velour material to promote ingrowth of the pad into the puncture site area. Pads, or felt pledgets, are commonly made of a felted polyester and may be cut to any suitable size or shape, such as those available from Bard® as PTFE Felt Pledgets having a nominal thickness of 2.87 mm. In some embodiments, the pad is larger in diameter than the rigid suturing disk (as described in PCT application '049218.

The sleeve gasket can function to seal any gap or leakage that may occur between the pad and the suturing disk. The sleeve gasket is made of a flexible material so that it can be compressed when the disk and/or pad are tightened against the puncture site, e.g. against the ventricular wall. The sleeve gasket may be connected to the pad and the disk as an integral assemblage, or the components may be separately slid onto the suturing tether, in order, and then tightened against the puncture site, e.g. ventricular wall. The sleeve gasket can function to prevent hemodynamic leakage that may flow along the path of the axially located suturing tether. Such anchoring tethers are used in deployment of prosthetic heart valves and typically extend from within the lumen of the organ being anchored, e.g. the heart, to the external anchoring location, e.g. the epicardial surface. Such epicardial pads may also be used to anchor one or more suturing tethers in other surgical situations where such tether(s) is required to extend from an intraluminal cavity to an external anchoring site.

The rigid suturing disk can function to provide the anchoring and mounting platform to which one or more suturing tethers may be tied. The disk may be made of any suitable biocompatible material. In some embodiments, the disk is made of polyethylene, or other hard or semi-hard polymer, and is covered with a polyester velour to promote ingrowth. In other embodiments, it is made of metal such as Nitinol®, or ceramic materials. The disk can range in size depending on the particular need. In some embodiments, the size of the disk can range from 1.0-3.0 cm in diameter. In other embodiments, the size of the disk ranges from 0.2-5.0 cm; the larger size not necessarily for intraventricular anchoring but for other surgical use, e.g. hernia repair, gastrointestinal repairs, etc.

One benefit of using a disk as described above to capture and anchor a suture is that, unlike suture anchors that bore into tissue with screws or barbs, there is little or no trauma to the tissue at the site of the anchor. Further, using a disk, which quickly slides over the tether, instead of stitches, allows for the effective permanent closure of large punctures. Surgically closing large punctures by sewing takes time and is difficult. When closing a puncture in the heart, adding the difficulty of requiring a surgeon to sew the puncture closed can increase the likelihood of life threatening complications to the patient. This is especially so in situations where a prosthetic heart valve is delivered and deployed without opening the chest cavity using transcatheter technologies. Sewing a ventricular puncture closed in this situation is typically not tenable.

The disk may also have a channel on its sidewall to allow the tether to be wound around the disk to improve anchoring. This radial channel functions to allow a user to quickly capture and seat a suture tether that is intended to be anchored. A winding channel allows a user to quickly wind suture tether(s) around the disk. Using the winding channel in conjunction with the radial channel(s) allows a user to quickly anchor the suture, while permitting the user to unwind and recalibrate so that the tether tension is appropriate for the particular situation. In some embodiments, a suture that anchors a transcatheter valve will have about 2 lbs. of longitudinal force.

In one embodiment, the tether extends through the flexible pad, sleeve gasket, and rigid suturing disk, and the pad device is applied to the puncture site and makes contact with the epicardial surface. The tether may be trimmed after it is affixed to the disk. In another embodiment, the pad device has a locking pin. The locking pin functions to hold the suturing tether in place after the disk is tightened against the ventricular wall by piercing the tether as it travels axially through the disk. A locking pin hole on the disk allows the locking pin to laterally intersect and affix the longitudinally disposed suturing tether. In another embodiment, the anti-leakage sleeve is unnecessary and not included. In yet another embodiment, the flexible pad is unnecessary and not included. In another embodiment, the suturing disk may have an axial tunnel or aperture which is tapered to allow the suture to be easily threaded into the axial tunnel and to reduce lateral cutting force of the disk against the suture.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

What is claimed is:

1. An apparatus, comprising:
   a handle assembly;
   a tube assembly including an outer tube member defining a lumen and a coupling member coupled to a distal end portion of the outer tube member;
   a needle assembly configured to be received through the lumen of the outer tube member, the needle assembly including an elongate needle having a distal tip configured to be inserted through the epicardial surface of a heart and extend within the left ventricle of the heart; and
   an imaging probe coupled to the coupling member, the imaging probe including a cable and an imaging element disposed at, and directly coupled to, a distal end portion of the cable, the imaging probe configured to provide image data associated with a location of a commissural-commissural (C-C) plane and a location of the anterior-posterior (A-P) plane of the mitral valve and the annular region of the heart such that a prosthetic mitral valve can be deployed and positioned within the heart based at least in part on the C-C plane and the A-P plane,
   wherein the cable includes a proximal end portion coupled to the handle assembly and an intermediate portion extending between the proximal end portion and the distal end portion, the intermediate portion of the cable being positioned within the outer tube member, the distal end portion of the cable exiting a distal end of the outer tube member so that the distal end portion of the cable of the imaging probe forms a targeting loop configured to contact a portion of the epicardial surface to help stabilize the needle assembly when inserted into the heart, the targeting loop configured to define an aperture through which the elongate needle is configured to travel.

2. The apparatus of claim 1, wherein the imaging element of the imaging probe includes at least one ultrasound transducer.

3. The apparatus of claim 1, wherein the imaging element of the imaging probe includes a side-looking multi-element phased array transducer.

4. The apparatus of claim 3, wherein the phased-array transducer is configured to operate at a frequency ranging from about 5.0 to about 8.5 MHz.

5. The apparatus of claim 3, wherein the phased-array transducer is configured to provide at least one of greyscale imaging, color doppler imaging, tissue imaging, or 3D localization.

6. The apparatus of claim 1, wherein the imaging probe is configured to provide multi-direction steerability.

7. The apparatus of claim 1, further comprising:
   a prosthetic valve delivery device configured to deploy and align the prosthetic mitral valve within the heart, the alignment of the prosthetic mitral valve being based at least in part on the C-C plane and the A-P plane determined by the image data.

8. The apparatus of claim 7, further comprising:
   a self-expanding prosthetic mitral valve disposable within a lumen of the delivery device.

9. The apparatus of claim 7, further comprising:
   an epicardial pad, the epicardial pad configured to be secured to a tether coupled to the prosthetic mitral valve extending outside the epicardial surface of the heart when the prosthetic mitral valve has been deployed within the heart.

10. The apparatus of claim 7, wherein the needle assembly includes a needle tube defining a lumen, the apparatus further comprising:
    a guidewire configured to be received through the lumen of the needle tube and advanced into the left ventricle of the heart; and
    a dilator configured to be disposed over the guide wire and inserted into the left ventricle of the heart.

* * * * *